(12) United States Patent
Bertheleme et al.

(10) Patent No.: US 8,173,820 B2
(45) Date of Patent: May 8, 2012

(54) COMPOUNDS WHICH POTENTIATE THE AMPA RECEPTOR AND USES THEREOF IN MEDICINE

(75) Inventors: Nicolas Bertheleme, Harlow (GB); Wai Ngor Chan, Harlow (GB); Jaqueline Sandra Scott, Harlow (GB); Simon E. Ward, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 156 days.

(21) Appl. No.: 12/808,197

(22) PCT Filed: Dec. 17, 2008

(86) PCT No.: PCT/EP2008/067681
§ 371 (c)(1),
(2), (4) Date: Jun. 15, 2010

(87) PCT Pub. No.: WO2009/080637
PCT Pub. Date: Jul. 2, 2009

(65) Prior Publication Data
US 2011/0021578 A1    Jan. 27, 2011

(30) Foreign Application Priority Data

Dec. 19, 2007 (GB) .................................. 0724783.6
Oct. 2, 2008 (GB) .................................. 0818068.9

(51) Int. Cl.
*C07D 211/72* (2006.01)
*C07D 213/62* (2006.01)
*C07C 303/00* (2006.01)
*A61K 31/44* (2006.01)
*A61K 31/16* (2006.01)

(52) U.S. Cl. .......... 546/290; 546/301; 564/99; 514/345; 514/606

(58) Field of Classification Search .................. None
See application file for complete search history.

(56) References Cited

U.S. PATENT DOCUMENTS
6,525,099 B1    2/2003    Arnold et al.

FOREIGN PATENT DOCUMENTS
WO   WO 2006/015828   2/2006
WO   WO 2006/015829   2/2006

*Primary Examiner* — Janet Andres
*Assistant Examiner* — Heidi Reese
(74) *Attorney, Agent, or Firm* — Bonnie L. Deppenbrock

(57) ABSTRACT

Compounds of formula (I) and salts thereof are provided: wherein n is 0, 1, 2 or 3; $R^1$ is selected from phenyl and pyridyl, each of which is optionally substituted by one or two groups independently selected from $C_{1-4}$alkyl and halogen; and $R^2$ is selected from H and $CH_3$ when n is 1 and $R^2$ is H when n is 2 or 3. Processes for preparation, pharmaceutical compositions, and uses thereof as a medicament, for example in the treatment of a disease or condition mediated by a reduction or imbalance in glutamate receptor function, such as schizophrenia or cognition impairment, are also disclosed.

(I)

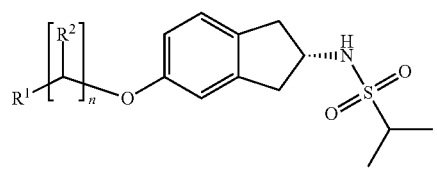

9 Claims, No Drawings

COMPOUNDS WHICH POTENTIATE THE AMPA RECEPTOR AND USES THEREOF IN MEDICINE

This application is a 371 of International Application No. PCT/EP2008/067681, filed 17 Dec. 2008, which claims the priority of GB Application No. GB 0818068.9 filed 2 Oct. 2008 and GB Application No. GB 0724783.6 filed 19 Dec. 2007, which are incorporated herein in their entirety.

This invention relates to novel compounds which potentiate the AMPA receptor. The invention also relates to the use of the compounds in treating diseases and conditions mediated by potentiation of the glutamate receptor, compositions containing the derivatives and processes for their preparation.

Glutamate receptors, which mediate the majority of fast excitatory neurotransmission in the mammalian central nervous system (CNS), are activated by the excitatory amino acid, L-glutamate (for review see Watkins J C, Krogsgaard-Larsen P, Honore T (1990) Trends Pharmacol Sci 11: 25-33).

Glutamate receptors can be divided into two distinct families. The G-protein or second messenger-linked "metabotropic" glutamate receptor family which can be subdivided into three groups (Group I, mGlu1 and mGlu5; Group II, mGlu2 and mGlu3; Group III, mGlu4, mGlu6, mGlu7, mGlu8) based on sequence homology and intracellular transduction mechanisms (for review see Conn P J and Pinn J P (1997) Ann Rev Pharmacol Toxicol 37: 205-237). The "ionotropic" glutamate receptor family, which directly couple to ligand-gated cation channels, can be subdivided into at least three subtypes based on depolarizing activation by selective agonists, N-methyl-D-aspartate (NMDA), α-amino-3-hydroxy-5-methylisoxazole-4-propionic acid (AMPA) and kainic acid (KA) (for review see Dingledine R, Borges K, Bowie D and Traynelis S (1999) Pharmacol. Rev. 51: 7-61).

Native AMPA receptors (AMPAR) exist as heterotetramers consisting of combinations of four different protein subunits (GluR1-4) (for review see Bettler B and Muller C (1995) Neuropharmacology 34: 123-139). Receptor subunit diversity is increased further as each subunit can undergo alternative splicing of a 38 amino acid sequence in the extracellular region just before the fourth membrane spanning domain M4. Such editing results in so-called 'flip' and 'flop' receptor isoforms which differ in kinetic and pharmacological properties (Sommer B, Keinanen K, Verdoon T A, Wisden W, Burnashev N, Herb A, Kohler M, Takagi T, Sakmann B, Seeburg P H (1990) Science 249: 1580-1585).

Additionally, post-transcriptional editing of GluR2 mRNA changes a neutral glutamine to a positively charged arginine within M2. In normal humans>99% GluR2 is edited in this way. AMPAR containing such edited GluR2 subunit exhibit low calcium permeability (Burnachev N, Monyer H, Seeburg P H, Sakmann B (1992) Neuron 8: 189-198). There is a suggestion, however, that the number of AMPAR with high calcium permeability is elevated in certain disease-associated conditions (Weiss J H, and Sensi S L (2000) Trends in Neurosci 23: 365-371).

AMPAR depolarization removes voltage dependent $Mg^{2+}$ block of NMDA receptors which in turn leads to NMDA receptor activation, an integral stage in the induction of Long Term Potentiation ("LTP") (Bliss T V P, Collingridge G L (1993) Nature 361: 31-9). LTP is a physiological measure of increased synaptic strength following a repetitive stimulus or activity, such as occurs during learning.

It has been reported that direct activation of glutamate receptors by agonists, in conditions where glutamate receptor function is reduced, increases the risk of excitotoxicity and additional neuronal damage. AMPAR positive allosteric modulators do not activate the receptor directly. However, when the ligand (L-glutamate or AMPA) is present AMPAR modulators increase receptor activity. Thus, AMPA receptor modulators enhance synaptic function when glutamate is released and is able to bind at post-synaptic receptor sites.

Compounds which act as AMPAR positive allosteric modulators have been shown to increase ligand affinity for the receptor (Arai A, Guidotti A, Costa E, Lynch G (1996) Neuroreport. 7: 2211-5); reduce receptor desensitization and reduce receptor deactivation (Arai A C, Kessler M, Rogers G, Lynch G (2000) 58: 802-813) and facilitate the induction of LTP both in vitro (Arai A, Guidotti A, Costa E, Lynch G (1996) 7: 2211-5) and in vivo (Staubli U, Perez Y, Xu F, Rogers G, Ingvar M, Stone-Elander S, Lynch G (1994) Proc Natl Acad Sci 91: 11158-11162). Such compounds also enhance the learning and performance of various cognitive tasks in rodent (Zivkovic I, Thompson D M, Bertolino M, Uzunov D, DiBella M, Costa E, Guidotti A (1995) JPET 272: 300-309, Lebrun C, Pilliere E, Lestage P (2000) Eu J Pharmacol 401: 205-212), sub-human primate (Thompson D M, Guidotti A, DiBella M, Costa E (1995) Proc Natl Acad Sci 92: 7667-7671) and man (Ingvar M, Ambros-Ingerson J, Davis M, Granger R, Kessler M, Rogers G A, Schehr R S, Lynch G (1997) Exp Neurol 146: 553-559). The efficacy of various AMPAR positive allosteric modulators in pre-clinical and clinical models of psychiatric disorders, such as schizophrenia, have been investigated (Morrow J A, Maclean J K F, Jamieson C (2006) Current Opinion in Drug Discovery and Development 9(5) 571-579).

Compounds which act as AMPA receptor positive allosteric modulators are known, for example in international patent application WO2006/015828.

We have discovered novel compounds which potentiate the AMPA receptor.

In the first aspect, the present invention provides a compound of formula (I) or a salt thereof:

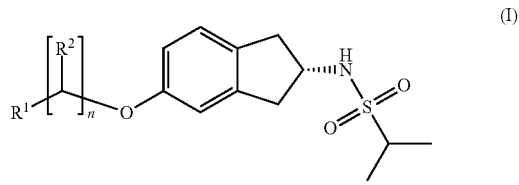

wherein:
n is 0, 1, 2 or 3;
R¹ is selected from phenyl and pyridyl, each of which is optionally substituted by one or two groups independently selected from $C_{1-4}$alkyl and halogen; and
R² is selected from H and $CH_3$ when n is 1; and R² is H when n is 2 or 3.

The term "halogen" refers to fluoro, chloro, bromo or iodo. In one embodiment, halogen is fluoro.

The term "$C_{1-4}$alkyl" refers to an alkyl group having from one to four carbon atoms. Unless otherwise indicated, $C_{1-4}$alkyl may be a straight chain or branched alkyl group. For example, a $C_{1-4}$alkyl group may be selected from the group consisting of methyl, ethyl, n-propyl, i-propyl, n-butyl, i-butyl and t-butyl. For example, $C_{1-4}$alkyl is methyl.

"Pyridyl" is interchangeable with "pyridinyl".

In one embodiment, n is 0. In another embodiment, n is 1 and R² is H. In a further embodiment, n is 2. In a yet further embodiment, n is 3. In one embodiment, R² is H and n is 1, 2 or 3.

In one embodiment, R¹ is phenyl.

When R¹ is pyridyl, it may be a 2-pyridyl, 3-pyridyl or 4-pyridyl. In one embodiment, R¹ is a 2-pyridyl or 3-pyridyl, each optionally substituted by one or two groups independently selected from $C_{1-4}$alkyl and halogen.

In one embodiment, R¹ is pyridyl, optionally substituted by a halogen (such as fluoro) or by one or two $C_{1-4}$alkyl groups (such as methyl). In one embodiment, R¹ is pyridyl, optionally substituted by a halogen (such as fluoro) or a $C_{1-4}$alkyl group (such as methyl). In one embodiment, R¹ is pyridyl, optionally substituted by one or two $C_{1-4}$alkyl. In one embodiment, R¹ is pyridyl, optionally substituted by one or two methyl.

In one embodiment, the present invention provides a compound of formula (Ia) or a salt thereof:

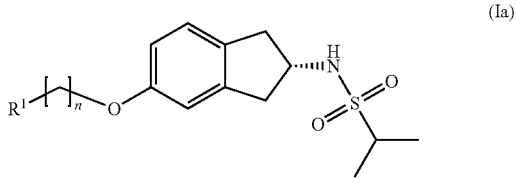

wherein:
n is 0 or 1; and
R¹ is selected from phenyl and pyridyl, each of which is optionally substituted by one or two groups independently selected from $C_{1-4}$alkyl and halogen.

In a further embodiment, the invention provides a compound of formula (Ia) or a salt thereof wherein:
n is 0 or 1; and
R¹ is pyridyl, optionally substituted by a group selected from $C_{1-4}$alkyl and halogen.

In a further embodiment, the invention provides a compound of formula (Ia) or a salt thereof wherein:
n is 0 or 1; and
R¹ is pyridyl, optionally substituted by one or two methyl.

All references to compounds of formula (I) include compounds of formula (Ia).

For the avoidance of doubt, unless otherwise indicated, the term "substituted" means substituted by one or more defined groups. In the case where groups may be selected from a number of alternative groups, the selected groups may be the same or different. For the avoidance of doubt, the term "independently" means that where more than one substituent is selected from a number of possible substituents, those substituents may be the same or different.

It will be appreciated that the present invention is intended to include compounds having any combination of the groups listed hereinbefore. It will be understood that, where appropriate, an embodiment described above for one part of the invention may be combined with an embodiment of another part of the invention.

In one embodiment, the compound is:
N-[(2S)-5-(phenyloxy)-2,3-dihydro-1H-inden-2-yl]-2-propanesulfonamide;
N-{(2S)-5-[(2-pyridinylmethyl)oxy]-2,3-dihydro-1H-inden-2-yl}-2-propanesulfonamide;
N-{(2S)-5-[(6-methyl-3-pyridinyl)oxy]-2,3-dihydro-1H-inden-2-yl}-2-propanesulfonamide;
N-[(2S)-5-(2-pyridinyloxy)-2,3-dihydro-1H-inden-2-yl]-2-propanesulfonamide;
N-{(2S)-5-[(5-fluoro-2-pyridinyl)oxy]-2,3-dihydro-1H-inden-2-yl}-2-propanesulfonamide;
N-{(2S)-5-[(2-methyl-3-pyridinyl)oxy]-2,3-dihydro-1H-inden-2-yl}-2-propanesulfonamide;
N-((2S)-5-{[(2-methyl-3-pyridinyl)methyl]oxy}-2,3-dihydro-1H-inden-2-yl)-2-propanesulfonamide;
N-{(2S)-5-[(4-methyl-3-pyridinyl)oxy]-2,3-dihydro-1H-inden-2-yl}-2-propanesulfonamide;
N-((2S)-5-{[(6-methyl-3-pyridinyl)methyl]oxy}-2,3-dihydro-1H-inden-2-yl)-2-propanesulfonamide;
N-{(2S)-5-[(3-pyridinylmethyl)oxy]-2,3-dihydro-1H-inden-2-yl}-2-propanesulfonamide;
or a salt thereof.

In one embodiment, the compound is:
N-((2S)-5-{[3-(3-pyridinyl)propyl]oxy}-2,3-dihydro-1H-inden-2-yl)-2-propanesulfonamide;
N-((2S)-5-{[3-(6-methyl-3-pyridinyl)propyl]oxy}-2,3-dihydro-1H-inden-2-yl)-2-propanesulfonamide;
N-{(2S)-5-[(6-methyl-2-pyridinyl)oxy]-2,3-dihydro-1H-inden-2-yl}-2-propanesulfonamide;
N-{(2S)-5-[(5-methyl-2-pyridinyl)oxy]-2,3-dihydro-1H-inden-2-yl}-2-propanesulfonamide;
N-{(2S)-5-[(4-methyl-2-pyridinyl)oxy]-2,3-dihydro-1H-inden-2-yl}-2-propanesulfonamide;
N-((2S)-5-{[2-(3-pyridinyl)ethyl]oxy}-2,3-dihydro-1H-inden-2-yl)-2-propanesulfonamide;
N-((2S)-5-{[(2,6-dimethyl-3-pyridinyl)methyl]oxy}-2,3-dihydro-1H-inden-2-yl)-2-propanesulfonamide;
N-{(2S)-5-[(4-pyridinylmethyl)oxy]-2,3-dihydro-1H-inden-2-yl}-2-propanesulfonamide;
N-((2S)-5-{[(2-methyl-4-pyridinyl)methyl]oxy}-2,3-dihydro-1H-inden-2-yl)-2-propanesulfonamide;
N-((2S)-5-{[(1S)-1-(6-methyl-3-pyridinyl)ethyl]oxy}-2,3-dihydro-1H-inden-2-yl)-2-propanesulfonamide;
N-((2S)-5-{[(1R)-1-(6-methyl-3-pyridinyl)ethyl]oxy}-2,3-dihydro-1H-inden-2-yl)-2-propanesulfonamide;
or a salt thereof.

In one embodiment, the compound is:
N-[(2S)-5-(phenyloxy)-2,3-dihydro-1H-inden-2-yl]-2-propanesulfonamide;
or a salt thereof.

In one embodiment, the compound is:
N-{(2S)-5-[(6-methyl-3-pyridinyl)oxy]-2,3-dihydro-1H-inden-2-yl}-2-propanesulfonamide;
N-[(2S)-5-(2-pyridinyloxy)-2,3-dihydro-1H-inden-2-yl]-2-propanesulfonamide;
N-{(2S)-5-[(5-fluoro-2-pyridinyl)oxy]-2,3-dihydro-1H-inden-2-yl}-2-propanesulfonamide;
N-{(2S)-5-[(2-methyl-3-pyridinyl)oxy]-2,3-dihydro-1H-inden-2-yl}-2-propanesulfonamide;
N-{(2S)-5-[(4-methyl-3-pyridinyl)oxy]-2,3-dihydro-1H-inden-2-yl}-2-propanesulfonamide;
N-{(2S)-5-[(6-methyl-2-pyridinyl)oxy]-2,3-dihydro-1H-inden-2-yl}-2-propanesulfonamide;
N-{(2S)-5-[(5-methyl-2-pyridinyl)oxy]-2,3-dihydro-1H-inden-2-yl}-2-propanesulfonamide;
N-{(2S)-5-[(4-methyl-2-pyridinyl)oxy]-2,3-dihydro-1H-inden-2-yl}-2-propanesulfonamide;
or a salt thereof.

In one embodiment, the compound is:
N-{(2S)-5-[(2-pyridinylmethyl)oxy]-2,3-dihydro-1H-inden-2-yl}-2-propanesulfonamide;
N-((2S)-5-{[(2-methyl-3-pyridinyl)methyl]oxy}-2,3-dihydro-1H-inden-2-yl)-2-propanesulfonamide;
N-((2S)-5-{[(6-methyl-3-pyridinyl)methyl]oxy}-2,3-dihydro-1H-inden-2-yl)-2-propanesulfonamide;
N-{(2S)-5-[(3-pyridinylmethyl)oxy]-2,3-dihydro-1H-inden-2-yl}-2-propanesulfonamide;

N-((2S)-5-{[3-(3-pyridinyl)propyl]oxy}-2,3-dihydro-1H-inden-2-yl)-2-propanesulfonamide;
N-((2S)-5-{[3-(6-methyl-3-pyridinyl)propyl]oxy}-2,3-dihydro-1H-inden-2-yl)-2-propanesulfonamide;
N-((2S)-5-{[2-(3-pyridinyl)ethyl]oxy}-2,3-dihydro-1H-inden-2-yl)-2-propanesulfonamide;
N-((2S)-5-{[(2,6-dimethyl-3-pyridinyl)methyl]oxy}-2,3-dihydro-1H-inden-2-yl)-2-propanesulfonamide;
N-{(2S)-5-[(4-pyridinylmethyl)oxy]-2,3-dihydro-1H-inden-2-yl}-2-propanesulfonamide;
N-((2S)-5-{[(2-methyl-4-pyridinyl)methyl]oxy}-2,3-dihydro-1H-inden-2-yl)-2-propanesulfonamide;
N-((2S)-5-{[(1S)-1-(6-methyl-3-pyridinyl)ethyl]oxy}-2,3-dihydro-1H-inden-2-yl)-2-propanesulfonamide;
N-((2S)-5-{[(1R)-1-(6-methyl-3-pyridinyl)ethyl]oxy}-2,3-dihydro-1H-inden-2-yl)-2-propanesulfonamide;
or a salt thereof.

In one embodiment, the compound is N-{(2S)-5-[(2-methyl-3-pyridinyl)oxy]-2,3-dihydro-1H-inden-2-yl}-2-propanesulfonamide or a salt thereof.

In one embodiment, the compound is N-{(2S)-5-[(2-methyl-3-pyridinyl)oxy]-2,3-dihydro-1H-inden-2-yl}-2-propanesulfonamide or the hydrochloride salt thereof.

In an embodiment there is provided a compound of formula (I) as defined above or a pharmaceutically acceptable salt thereof.

Salts of compounds of formula (I) which are suitable for use in medicine are those wherein the counterion is pharmaceutically acceptable. However, salts having non-pharmaceutically acceptable counterions are within the scope of the present invention, for example, for use as intermediates in the preparation of other compounds of formula (I) and their pharmaceutically acceptable salts and/or for use in non-therapeutic, for example, in vitro, situations.

As used herein, the term "salt" refers to any salt of a compound according to the present invention prepared from an inorganic or organic acid or base, quaternary ammonium salts and internally formed salts. Pharmaceutically acceptable salts are particularly suitable for medical applications because of their greater aqueous solubility relative to the parent compounds. Such salts must clearly have a pharmaceutically acceptable anion or cation. Suitably pharmaceutically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, (1R)-(−)-10-camphorsulphonic, (1S)-(+)-10-camphorsulphonic, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example naphthalene-1,5-disulphonic, naphthalene-1,3-disulphonic, benzenesulfonic, and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. The salts may have any suitable stoichiometry. For example, a salt may have 1:1 or 2:1 stoichiometry. Non-integral stoichiometry ratios are also possible.

In an embodiment there is provided a compound of formula (I) as defined above or a hydrochloride salt thereof.

Solvates of the compounds of formula (I) and solvates of the salts of the compounds of formula (I) are included within the scope of the present invention. As used herein, the term "solvate" refers to a complex of variable stoichiometry formed by a solute (in this invention, a compound of formula (I) or a salt thereof) and a solvent. Those skilled in the art of organic chemistry will appreciate that many organic compounds can form such complexes with solvents in which they are reacted or from which they are precipitated or crystallized. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water. Where the solvent used is water such a solvate may then also be referred to as a hydrate.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may be administered as prodrugs. Examples of pro-drug forms for certain compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention. Examples of prodrugs for certain compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Hereinafter, compounds of formula (I) (whether in solvated or unsolvated form) or their pharmaceutically acceptable salts (whether in solvated or unsolvated form) or prodrugs thereof defined in any aspect of the invention (except intermediate compounds in chemical processes) are referred to as "compounds of the invention".

Also included within the scope of the invention are polymorphs of a compound of the invention.

The invention also includes all suitable isotopic variations of a compound of the invention. An isotopic variation of a compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the invention, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples hereafter using appropriate isotopic variations of suitable reagents.

Compounds of the present invention have an S stereochemistry at the 2-position of the 1H-inden-2-yl group. Compounds of the present invention where n is 0, 2 or 3 or where n is 1 and R$^2$ is H are in the S enantiomeric form. The different forms (R and S) may be separated one from the other by the usual methods, or may be obtained by stereospecific or asymmetric synthesis. For the Example compounds of the present invention shown below, the chiral intermediate (2S)-5-bromo-2-aminoindane was first prepared:

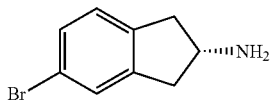

using (1R)-(−)-10-camphorsulphonic acid as the resolving agent, as disclosed in Prashad et al, *Adv. Synth. Catal.* 2001, 343, No. 5, pp 461-472 and also described in WO 2006/015828. The absolute configuration of (2S)-5-bromo-2-aminoindane (1R)-(−)-10-camphorsulphonic acid salt so obtained has been confirmed by single crystal X-ray analysis.

Compounds of the present invention where n is 1 and R$^2$ is CH$_3$ may exist in two diastereomeric forms both of which are within the scope of the present invention. For example, N-((2S)-5-{[1-(6-methyl-3-pyridinyl)ethyl]oxy}-2,3-dihydro-1H-inden-2-yl)-2-propanesulfonamide may be either the N-((2S)-5-{[(1R)-1-(6-methyl-3-pyridinyl)ethyl]oxy}-2,3-dihydro-1H-inden-2-yl)-2-propanesulfonamide stereoisomer, the N-((2S)-5-{[(1S)-1-(6-methyl-3-pyridinyl)ethyl]oxy}-2,3-dihydro-1H-inden-2-yl)-2-propanesulfonamide stereoisomer or a mixture of diastereomers.

In one embodiment a compound of the invention has at least 80% e.e. In another embodiment, a compound of the invention has at least 90% e.e., for example at least 95% e.e. In another embodiment the isomer corresponds to at least 98% e.e, for example at least 99% e.e.

Since the compounds of the invention are intended for use in pharmaceutical compositions it will readily be understood that they are each optionally provided in substantially pure form, for example at least 60% pure, for example at least 75% pure or at least 85%, or at least 98% pure (% are on a weight for weight basis). Impure preparations of the compounds may be used for preparing the more pure forms used in the pharmaceutical compositions; these less pure preparations of the compounds should contain at least 1%, or at least 5% or from 10 to 59% of a compound of the invention.

Compounds of the invention may be prepared by methods known in the art of organic synthesis as set forth in part by the following synthesis schemes. In the following reaction schemes and hereafter, unless otherwise stated, all the groups are as defined in the first aspect. It is also recognised that in all of the schemes described below, it is well understood that protecting groups for sensitive or reactive groups are employed where necessary in accordance with general principles of chemistry. Protecting groups are manipulated according to standard methods of organic synthesis (T. W. Greene and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of the invention.

Scheme 1 below illustrates the preparation of a compound of formula (Ib) (which is a compound of formulas wherein n is 0) by reaction with the appropriate alcohol ArOH. Typical reaction conditions comprise microwaving at a suitable temperature, for example 190 degC, a mixture of a compound of formula (II) and the required alcohol, for example phenol, in the presence of a suitable copper reagent such as copper (I) iodide, a suitable ligand such as N,N-dimethylglycine, and a suitable base such as caesium carbonate in a suitable solvent such as dimethylsulphoxide for the required time, for example 30 minutes. Alternatively, the above mixture may be heated under argon using a heating block or oil bath for the appropriate time and temperature, for example 30 hours at 130 degC. The preparation of a compound of formula (II) where X=Br is detailed in the experimental section. Alcohols R$^1$OH are commercially available or may be prepared by methods described in the literature.

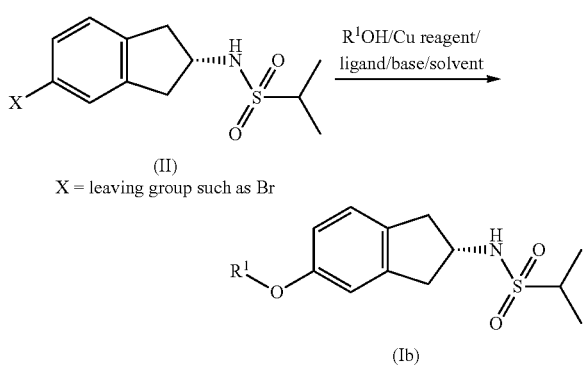

Alternatively, a compound of formula (Ib) may be prepared from a compound of formula (III) by reaction with the appropriate halide R$^1$X according to scheme 2. Typical reaction conditions comprise microwaving at a suitable temperature, for example 190 degC, a mixture of a compound of formula (III) and the required halide, for example 2-bromopyridine, in the presence of a suitable copper reagent such as copper (I) iodide, a suitable ligand such as N,N-dimethylglycine, and a suitable base such as caesium carbonate in a suitable solvent such as dimethylsulphoxide for the required time, for example 30 minutes. Alternatively, the above mixture may be heated under argon using a heating block or oil bath for the appropriate time and temperature, for example 30 hours at 130 degC. The preparation of a compound of formula (III) is detailed in the experimental section. Halides R$^1$X are commercially available or may be prepared by methods described in the literature.

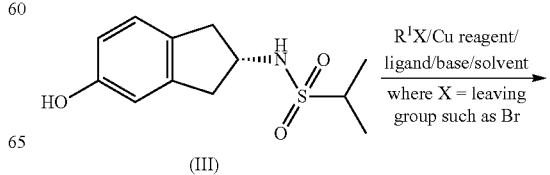

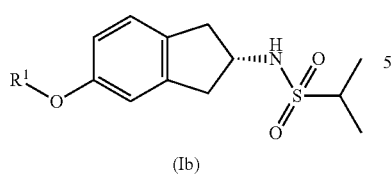

(Ib)

A compound of formula (Ic) shown below may be prepared from a compound of formula (III) by the Mitsunobu reaction with the appropriate alcohol $R^1(CH_2)_nOH$ according to scheme 3. Typical reaction conditions comprise adding a phosphine reagent such as triphenylphosphine then a suitable azodicarboxylate reagent such as diisopropyl azodicarboxylate to a mixture of a compound of formula (III) and the appropriate alcohol such as 2-pyridinylmethanol in a suitable solvent such as dichloromethane at a suitable temperature such as ambient under argon and mixing for the required time, such as 16 hours. The preparation of a compound of formula (III) is detailed in the experimental section. Alcohols $R^1(CH_2)_nOH$ are commercially available or may be prepared by methods described in the literature.

Scheme 3

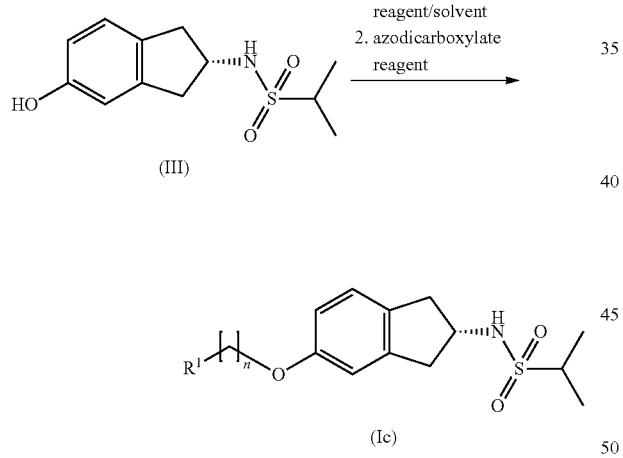

where n is 1, 2 or 3

Alternatively, a compound of formula (Ic) shown below may be prepared from a compound of formula (III) by alkylation with the appropriate chloride $R^1(CH_2)_nCl$ according to scheme 4. Typical reaction conditions comprise adding a base such as cesium carbonate, an activator such as potassium iodide and the appropriate chloride $R^1(CH_2)_nCl$ to a compound of formula (III) in a suitable solvent such as N,N-dimethylformamide at a suitable temperature such as ambient and mixing for the required time, such as 24 hours. The preparation of a compound of formula (III) is detailed in the experimental section. Halides $R^1(CH_2)_nCl$ are commercially available or may be prepared by methods described in the literature.

Scheme 4

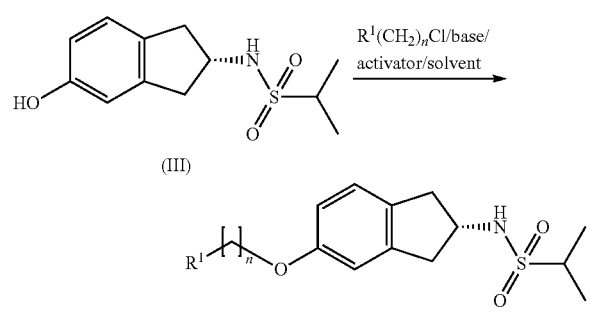

where n is 1, 2 or 3

A compound of formula (Id) shown below may be prepared from a compound of formula (III) by the Mitsunobu reaction with the appropriate alcohol $R^1CH(CH_3)OH$ according to scheme 5. Typical reaction conditions comprise adding a phosphine reagent such as triphenylphosphine then a suitable azodicarboxylate reagent such as diisopropyl azodicarboxylate to a mixture of a compound of formula (III) and the appropriate alcohol such as 1-(6-methyl-3-pyridinyl)ethanol in a suitable solvent such as dichloromethane at a suitable temperature such as ambient under argon and mixing for the required time, such as 16 hours. The preparation of a compound of formula (III) is detailed in the experimental section. Alcohols $R^1CH(CH_3)OH$ are commercially available or may be prepared by methods described in the literature.

Scheme 5

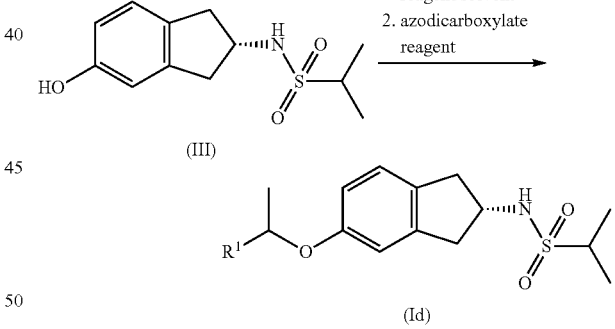

Salts may be prepared conventionally by reaction with the appropriate acid or acid derivative.

Further details for the preparation of compounds of formula (I) are found in the Examples section hereinafter.

The compounds of the invention may be prepared singly or as compound libraries comprising at least 2, for example 5 to 1,000 compounds, for example 10 to 100 compounds. Libraries of compounds of the invention may be prepared by a combinatorial 'split and mix' approach or by multiple parallel synthesis using either solution phase or solid phase chemistry, by procedures known to those skilled in the art. Thus according to a further aspect there is provided a compound library comprising at least 2 compounds of the invention.

The compounds of the present invention potentiate the AMPA receptor, as measured by the assays below. Compounds which potentiate the AMPA receptor are potentially useful for treating diseases and conditions which are mediated by the potentiation of the glutamate receptor.

The present invention provides a compound of formula (I) or a pharmaceutically acceptable salt thereof for use in medicine.

In one embodiment, the present invention provides a compound of formula (I) or a pharmaceutically acceptable salt thereof for use in treating a disease or condition mediated by a reduction or imbalance in glutamate receptor function in a mammal.

The present invention also provides a pharmaceutical composition comprising a compound of formula (I) or a pharmaceutically acceptable salt thereof and at least one carrier, diluent or excipient. The present invention also provides a pharmaceutical composition comprising 0.05 to 1000 mg of a compound of formula (I) or a pharmaceutically acceptable salt thereof and 0.1 g to 2 g of at least one pharmaceutically acceptable carrier or diluent. The present invention also provides a pharmaceutical composition for the treatment of schizophrenia comprising a compound of formula (I) or a pharmaceutically acceptable salt thereof.

It will be appreciated that the invention includes the following further aspects. The embodiments described in respect of the first aspect apply equally to each of these further aspects:

i) the use of a compound of formula (I) or a pharmaceutically acceptable salt thereof in the manufacture of a medicament for treating a disease or condition mediated by a reduction or imbalance in glutamate receptor function in a mammal;
ii) a compound of formula (I) or a pharmaceutically acceptable salt thereof for use in treating a disease or condition mediated by a reduction or imbalance in glutamate receptor function in a mammal;
iii) a method of treatment of a disease or condition mediated by a reduction or imbalance in glutamate receptor function in a mammal comprising administering an effective amount of a compound of formula (I) or a pharmaceutically acceptable salt thereof;
iv) a combination product of a compound of formula (I) or a pharmaceutically acceptable salt thereof with an antipsychotic;
v) a pharmaceutical composition comprising a combination product as defined in iv) above and at least one carrier, diluent or excipient;
vi) the use of a combination product as defined in iv) above in the manufacture of a medicament for treating a disease or condition mediated by a reduction or imbalance in glutamate receptor function in a mammal;
vii) a combination product as defined in iv) above for use in treating a disease or condition mediated by a reduction or imbalance in glutamate receptor function in a mammal;
viii) a combination product as defined in iv) above for use as a medicament;
ix) a method of treatment of a disease or condition mediated by a reduction or imbalance in glutamate receptor function in a mammal comprising administering an effective amount of a combination product as defined in iv) above.

Relevant diseases or conditions are: psychosis and psychotic disorders (including schizophrenia, schizo-affective disorder, schizophreniform diseases, brief reactive psychosis, child onset schizophrenia, "schizophrenia-spectrum" disorders such as schizoid or schizotypal personality disorders, acute psychosis, alcohol psychosis, drug-induced psychosis, autism, delerium, mania (including acute mania), manic depressive psychosis, hallucination, endogenous psychosis, organic psychosyndrome, paranoid and delusional disorders, puerperal psychosis, and psychosis associated with neurodegenerative diseases such as Alzheimer's disease); substance related disorders (including alcohol-related disorders and nicotine-related disorders); cognitive impairment (e.g. the treatment of impairment of cognitive functions including attention, orientation, memory (i.e. memory disorders, amnesia, amnesic disorders and age-associated memory impairment) and language function, and including cognitive impairment as a result of stroke, Alzheimer's disease, Aids-related dementia or other dementia states, as well as other acute or sub-acute conditions that may cause cognitive decline such as delirium or depression (pseudodementia states) trauma, aging, stroke, neurodegeneration, drug-induced states, neurotoxic agents), mild cognitive impairment, age related cognitive impairment, autism related cognitive impairment, Down's syndrome, cognitive deficit related to psychosis, post-electroconvulsive treatment related cognitive disorders; anxiety disorders (including generalised anxiety disorder, social anxiety disorder, agitation, tension, social or emotional withdrawal in psychotic patients, panic disorder, and obsessive compulsive disorder); neurodegenerative diseases (such as Alzheimer's disease, amyotrophic lateral sclerosis, motor neurone disease and other motor disorders such as Parkinson's disease (including relief from locomotor deficits and/or motor disability, including slowly increasing disability in purposeful movement, tremors, bradykinesia, hyperkinesia (moderate and severe), akinesia, rigidity, disturbance of balance and co-ordination, and a disturbance of posture), dementia in Parkinson's disease, dementia in Huntington's disease, neuroleptic-induced Parkinsonism and tardive dyskinesias, neurodegeneration following stroke, cardiac arrest, pulmonary bypass, traumatic brain injury, spinal cord injury or the like, and demyelinating diseases such as multiple sclerosis and amyotrophic lateral sclerosis); depression (which term includes bipolar (manic) depression (including type I and type II), unipolar depression, single or recurrent major depressive episodes with or without psychotic features, catatonic features, melancholic features, atypical features (e.g. lethargy, over-eating/obesity, hypersomnia) or postpartum onset, seasonal affective disorder and dysthymia, depression-related anxiety, psychotic depression, and depressive disorders resulting from a general medical condition including, but not limited to, myocardial infarction, diabetes, miscarriage or abortion); post-traumatic stress syndrome; attention deficit disorder; attention deficit hyperactivity disorder; drug-induced (phencyclidine, ketamine and other dissociative anaesthetics, amphetamine and other psychostimulants and cocaine) disorders; Huntingdon's chorea; tardive dyskinesia; dystonia; myoclonus; spasticity; obesity; stroke; sexual dysfunction; sleep disorders and some forms of epilepsy.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). Treatment of the various subtypes of the disorders mentioned herein using a compound of the present invention is contemplated as part of the present invention. Numbers in brackets after the listed diseases below refer to the classification code in DSM-IV.

Within the context of the present invention, the term "psychotic disorder" includes:—

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Compounds of the invention may also be of use in the treatment of the following disorders:—

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:

Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9):

Enhancement of cognition including the treatment of cognition impairment in other diseases such as schizophrenia, bipolar disorder, depression, other psychiatric disorders and psychotic conditions associated with cognitive impairment, e.g. Alzheimer's disease: and Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

All of the various forms and sub-forms of the disorders mentioned herein are contemplated as part of the present invention.

Within the context of the present invention, the term "cognitive impairment" includes for example the treatment of impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Alzheimer's disease, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, mild cognitive impairment, age related cognitive impairment, autism related cognitive impairment, Down's syndrome, cognitive deficit related to psychosis, and post-electroconvulsive treatment related cognitive disorders; and dyskinetic disorders such as Parkinson's disease, neuroleptic-induced parkinsonism, and tardive dyskinesias.

In one embodiment, the present invention provides a compound of the invention for use in treating schizophrenia or impairment of cognition.

In one embodiment, the present invention provides a use of a compound of the invention in the manufacture of a medicament for treating schizophrenia or impairment of cognition.

In one embodiment, the present invention provides a method of treating schizophrenia or impairment of cognition in a human, comprising administering an therapeutically effective amount of a compound of the present invention, alone or combined with a pharmaceutically acceptable carrier, dilutent or excipient.

The compounds of the invention may be used in combination with one or more of the following agents to treat psychotic disorders: i) antipsychotics (such as olanzapine, risperidone, clozapine, ziprazidone, talnetant); ii) drugs for extrapyramidal side effects, for example anticholinergics (such as benztropine, biperiden, procyclidine, trihexyphenidyl), antihistamines (such as diphenhydramine), dopaminergics (such as amantadine); iii) antidepressants; iv) anxiolytics; v) cognitive enhancers for example cholinesterase inhibitors (such as tacrine, donepezil, rivastigmine, galantamine).

The compounds of the invention may be used in combination with antidepressants to treat depression and mood disorders.

The compounds of the invention may be used in combination with one or more of the following agents to treat bipolar disease: i) mood stabilisers; ii) antipsychotics; iii) antidepressants.

The compounds of the invention may be used in combination with one or more of the following agents to treat anxiety disorders: i) anxiolytics; ii) antidepressants.

The compounds of the invention may be used in combination with one or more of the following agents to improve nicotine withdrawal and reduce nicotine craving: i) nicotine replacement therapy, for example a sublingual formulation of nicotine beta-cyclodextrin and nicotine patches; ii) drugs for treating nicotine addition, for example bupropion.

The compounds of the invention may be used in combination with one or more of the following agents to improve alcohol withdrawal and reduce alcohol craving: i) NMDA receptor antagonists for example acamprosate; ii) GABA receptor agonists for example tetrabamate; iii) Opioid receptor antagonists for example naltrexone.

The compounds of the invention may be used in combination with one or more of the following agents to improve opiate withdrawal and reduce opiate craving: i) opioid mu receptor agonist/opioid kappa receptor antagonist for example buprenorphine; ii) opioid receptor antagonists for example naltrexone; iii) vasodilatory antihypertensives for example lofexidine.

The compounds of the invention may be used in combination with one or more of the following agents to treat sleeping disorders: i) benzodiazepines for example temazepam, lormetazepam, estazolam, triazolam; ii) non-benzodiazepine hypnotics for example zolpidem, zopiclone, zaleplon, indiplon; iii) barbiturates for example aprobarbital, butabarbital, pentobarbital, secobarbita, phenobarbital; iv) antidepressants; v) other sedative-hypnotics for example chloral hydrate, chlormethiazole.

The compounds of the invention may be used in combination with one or more of the following agents to treat anorexia: i) appetite stimulants for example cyproheptidine; ii) antidepressants; iii) antipsychotics; iv) zinc; v) premenstrual agents for example pyridoxine and progesterones.

The compounds of the invention may be used in combination with one or more of the following agents to treat bulimia: i) antidepressants; ii) opioid receptor antagonists; iii) antiemetics for example ondansetron; iv) testosterone receptor antagonists for example flutamide; v) mood stabilisers; vi) zinc; vii) premenstrual agents.

The compounds of the invention may be used in combination with one or more of the following agents to treat autism: i) antipsychotics; ii) antidepressants; iii) anxiolytics; iv) stimulants for example methylphenidate, amphetamine formulations, pemoline.

The compounds of the invention may be used in combination with one or more of the following agents to treat Attention Deficit Hyperactivity Disorder: i) stimulants for example methylphenidate, amphetamine formulations, pemoline; ii) non-stimulants for example norepinephrine reuptake inhibitors (such as atomoxetine), alpha 2 adrenoceptor agonists (such as clonidine), antidepressants, modafinil, cholinesterase inhibitors (such as galantamine and donezepil).

The compounds of the invention may be used in combination with one or more of the following agents to treat personality disorders: i) antipsychotics; ii) antidepressants; iii) mood stabilisers; iv) anxiolytics.

The compounds of the invention may be used in combination with one or more of the following agents to treat male sexual dysfunction: i) phosphodiesterase V inhibitors, for example vardenafil, sildenafil; ii) dopamine agonists/dopamine transport inhibitors for example apomorphine, buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine; vii) 5-HT1A agonists, for example flibanserine.

The compounds of the invention may be used in combination with one or more of the following agents to treat female sexual dysfunction: i) the same agents specified for male sexual dysfunction, ii) an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone, amisulpride, ziprazidone and talnetant).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration to mammals including humans. The compositions may be formulated for administration by any route. The compositions may be formulated for oral, topical, or parenteral administration, and may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, for example water. The compound, depending on the vehicle and concentration used, can be either suspended or dissolved in the vehicle. In preparing solutions the compound can be dissolved in water for injection and filter sterilised before filling into a suitable vial or ampoule and sealing.

Agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. A surfactant or wetting agent may be included in the composition to facilitate uniform distribution of the compound.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e. the number of doses of a compound of the invention given per day for a defined number of days, can be ascertained by those skilled in the art using conventional course of treatment determination tests.

It is to be understood that "treatment" as used herein includes prophylaxis as well as alleviation of established symptoms. In one embodiment, the mammal to be treated is a human.

The invention is illustrated by the Examples described below.

Starting materials, reagents and solvents were obtained from commercial suppliers and used without further purification unless otherwise stated. Flash chromatography was carried out using pre-packed Isolute Flash™ or Biotage™ silica-gel columns as the stationary phase and analytical grade solvents as the eluent unless otherwise stated.

NMR spectra were obtained at 298K, 303.2K or 300K, at the frequency stated using either a Bruker™ DPX400 or AV400 machine or a Varian DirectDrive™ machine (operating at 500 MHz for acquiring proton NMR spectra) and run as a dilute solution of $CDCl_3$ unless otherwise stated. All NMR spectra were referenced to tetramethylsilane (TMS $\delta_H$ 0, $\delta_C$ 0). All coupling constants are reported in hertz (Hz), and multiplicities are labelled s (singlet), bs (broad singlet), d (doublet), t (triplet), q (quartet), dd (doublet of doublets), dt (doublet of triplets), td (triplet of doublets), ddd (double-double-doublet) and m (multiplet).

All quoted retention times are as measured using LC/MS (Liquid Chromatography/Mass Spectrometry). Where appropriate, these retention times were used as a guide for purification using mass-directed auto-purification (MDAP), which refers to purification by HPLC, wherein fraction collection is triggered by detection of the programmed mass ion for the compound of interest.

Total ion current traces were obtained for electrospray positive and negative ionisation (ES+/ES−) and/or atmospheric pressure chemical positive and negative ionisation (AP+/AP−).

Where reactions are described as having been carried out in a similar manner to earlier, more completely described reactions, the general reaction conditions used were essentially the same. Work up conditions used were of the types standard in the art, but may have been adapted from one reaction to another. The compounds may not necessarily have been prepared from the batch described herein. Unless otherwise stated, all compounds with chiral centre(s) are racemic. All reactions were either carried out under argon or may be carried out under argon, unless otherwise stated. Compounds synthesised may have various purities ranging from for example 85% to 98%. However, calculations of number of moles and yield are generally not adjusted for this.

ABBREVIATIONS

TEA Triethylamine
TMS-Cl Trimethylsilyl chloride
ss saturated solution
TFA Trifluoroacetic acid
DAD Diode Array Detector
CD Circular dichroism
a/a % percentage by area under the curve
LC/MS Liquid Chromatography/Mass Spectrometry
NMR Nuclear Magnetic Resonance
SCX strong cationic exchange
THF Tetrahydrofuran
DMSO Dimethylsulfoxide
DMF Dimethylformamide
DCM/MDC Dichloromethane/Methylene dichloride
CDI 1,1'-Carbonyldiimidazole
LDA Lithium diisopropylamide
EDC 1-ethyl-3-(dimethylaminopropyl)carbodiimide
MsCl Methanesulfonyl chloride
AcOH Acetic acid
HOAt 1-hydroxy-7-azabenzotriazole
HOBt 1-hydroxybenzotriazole
Pd on C Palladium on Charcoal
MeCN Acetonitrile
MDAP Mass-directed auto-purification
ES electrospray
min(s) minute(s)
$PdCl_2$(dppf) 1,1'-bis(diphenylphosphino)ferrocene palladium dichloride
DIAD diisopropyl azodicarboxylate
degC degrees Celsius
EtOAc ethyl acetate
HPLC/MS Ultra performance liquid chromatography/mass spectrometry
$Et_2O$ diethyl ether
MeOH methanol
Me methyl
Et ethyl
ppm parts per million
Analytical Chromatographic Conditions Unless otherwise stated, one of the following methods were used for the LC/MS analysis:

Method 1
Column: Waters Atlantis, 4.6 mm×50 mm. The stationary phase particle size is 3 um.
Solvents: A: Aqueous solvent=Water+0.05% Formic Acid; B: Organic solvent=Acetonitrile+0.05% Formic Acid
Methods: 5 minute runtime.

| Time/min | % B |
|---|---|
| 0 | 3 |
| 0.1 | 3 |
| 4 | 97 |
| 4.8 | 97 |
| 4.9 | 3 |
| 5.0 | 3 |

Flow rate: 3 ml/min
Infection volume: 5 µl
Column temperature: 30 degC
UV wavelength range: 220-330 nm
Method 1—High pH Version—as Above, Except:
Column: Waters X-Bridge 4.6 mm×50 mm. The stationary phase particle size is 3.5 µm.
A: Aqueous solvent=10 mM Ammonium Bicarbonate solution adjusted to pH 10 with ammonia solution.
B: Organic solvent=Acetonitrile.
Method 2
Column: Waters Acquity BEH HPLC C18, 2.1 mm×50 mm. The stationary phase particle size is 1.7 µm.
Solvents
A: Aqueous solvent=Water+0.05% Formic Acid
B: Organic solvent=Acetonitrile+0.05% Formic Acid
Weak Wash=1:1 Methanol: Water
Strong Wash=Water
The generic method used has a 2 minute runtime.

| Time/min | % B |
|---|---|
| 0 | 3 |
| 0.1 | 3 |
| 1.5 | 97 |
| 1.9 | 97 |
| 2.0 | 3 |

The above method has a flow rate of 1 ml/min.
The injection volume for the generic method is 0.5 ul
The column temperature is 40 degC
The UV detection range is from 220 to 330 nm
Formic Acid Generic Analytical HPLC/MS (ES+) Open Access 1.5 Minute Multi Step Method with Restricted Integration Window (Used for Descriptions 2, 3, 6 and 7 and Examples 6 (step 1), 7 and 9)
  LC/MS system: Acquity HPLC coupled with ZQ mass spectrometer
  The HPLC analysis was conducted on an Acquity HPLC BEH C18 column (2.1 mm×50 mm i.d. 1.7 µm particle size) at 40 degC.
  The injection volume was: 0.75 µl
  The solvents employed were:
  A=0.1% v/v solution of formic acid in water
  B=0.06% v/v solution of formic acid in acetonitrile
  The gradient employed was:

| Time (minutes) | % A | % B |
|---|---|---|
| 0 | 97 | 3 |
| 0.05 | 94.0 | 6.0 |
| 0.57 | 30.0 | 70.0 |
| 1.06 | 1.0 | 99.0 |
| 1.449 | 1.0 | 99.0 |
| 1.45 | 97.0 | 3.0 |

Stop time: 1.5 min
The flow rate was 1 ml/min.
UV Conditions
The UV detection was a summed signal from wavelength of 210 nm to 350 nm.
The acquisition rate was 20 Hz.
The integration of the DAD trace started at 0.3 min and ended at 1.50 min.
The DAD-MS Rt offset was 0.01 s.
MS Conditions
Ionisation mode: Positive Electrospray (ES+)
Scan Range: 100 to 1000 AMU
Scan Time: 0.20 s
Inter scan Delay: 0.08 s
Formic Acid Focus Analytical HPLC/MS (ES+) Open Access 1.5 Minute Multi Step Method (Used for Example 6 (Step 2)):
  LC/MS system: Acquity HPLC coupled with ZQ mass spectrometer
  The HPLC analysis was conducted on an Acquity HPLC BEH C18 column (2.1 mm×50 mm i.d. 1.7 µm particle size) at 40 degC.
  The injection volume was: 0.75 µl
  The solvents employed were:
  A=0.1% v/v solution of formic acid in water
  B=0.06% v/v solution of formic acid in acetonitrile
  The gradient employed was:

| Time (minutes) | % A | % B |
|---|---|---|
| 0 | 99 | 1 |
| 0.2 | 94.0 | 6.0 |
| 1.25 | 40.0 | 60.0 |
| 1.299 | 40.0 | 60.0 |
| 1.30 | 0.0 | 100.0 |

Stop time: 1.5 min
The flow rate was 1 ml/min.
UV Conditions
The UV detection was a summed signal from wavelength of 210 nm to 350 nm.
The acquisition rate was 20 Hz.
The integration of the DAD trace started at 0.3 min and ended at 1.45 min.
The DAD-MS Rt offset was 0.01 s.
MS Conditions
Ionisation mode: Positive Electrospray (ES+)
Scan Range: 100 to 1000 AMU
Scan Time: 0.20 s
Inter scan Delay: 0.08 s
High pH Generic Analytical HPLC Open Access LC/MS 5 Minute Method (Used for Example 19)
  The HPLC analysis was conducted on an XBridge C18 column (50 mm×4.6 mm i.d. 3.5 µm packing diameter) at 30 degC.

The solvents employed were:
A=10 mM ammonium bicarbonate in water adjusted to pH 10 with ammonia solution
B=acetonitrile
The gradient employed was:

| Time (minutes) | % A | % B |
|---|---|---|
| 0 | 99 | 1 |
| 0.1 | 99 | 1 |
| 4.0 | 3 | 97 |
| 5.0 | 3 | 97 |

The flow rate was 3 ml/min. The uv detection was an averaged signal from wavelength of 210 nm to 350 nm and mass spectra were recorded on a mass spectrometer using alternate-scan positive and negative mode electrospray ionisation.

Formic Acid Generic Analytical HPLC Open Access LC/MS 2 Minute Method (Used for Example 20):

The HPLC analysis was conducted on an Acquity HPLC BEH C18 column (2.1 mm×50 mm i.d. 1.7 μm packing diameter) at 40 degC.
The solvents employed were:
A=0.1% v/v solution of formic acid in water
B=0.1% v/v solution of formic acid in acetonitrile
The gradient employed was:

| Time (minutes) | % A | % B |
|---|---|---|
| 0 | 97 | 3 |
| 1.5 | 0 | 100 |
| 1.9 | 0 | 100 |
| 2.0 | 97 | 3 |

The flow rate was 1 ml/min. The uv detection was an averaged signal from wavelength of 210 nm to 350 nm and mass spectra were recorded on a mass spectrometer using alternate-scan positive and negative mode electrospray ionisation.

MDAP Conditions

Typical Conditions Used are Exemplified by:
Column: Waters Atlantis, 19 mm×100 mm (small scale) and 30 mm×100 mm (large scale). Stationary phase particle size=5 um.
Solvents: A: Aqueous solvent=Water+0.1% Formic Acid; B: Organic solvent=Acetonitrile+0.1% Formic Acid. Make up solvent=Methanol: Water 80:20. Needle rinse solvent=Methanol
Methods: There are five methods used depending on the analytical retention time of the compound of interest. They have a 13.5-minute runtime, which comprises of a 10-minute gradient followed by a 3.5 minute column flush and re-equilibration step.
Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)
Flow rate: 20 mls/min (Small Scale) or 40 mls/min (Large Scale).
High pH MDAP—as Above, Except for:

Column: Waters X-bridge, 30 mm×100 mm. The stationary phase particle size is 5 μm.
A: Aqueous solvent=10 mM Ammonium Bicarbonate solution adjusted to pH 10 with ammonia solution.
B: Organic solvent=Acetonitrile.
Make up solvent=Methanol: Water 80:20
Needle rinse solvent=Methanol Description 1: N-[(2S)-5-bromo-2,3-dihydro-1H-inden-2-yl]-2-propanesulfonamide

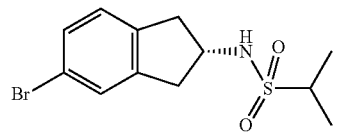

N-[(2S)-5-bromo-2,3-dihydro-1H-inden-2-yl]-2-propanesulfonamide was prepared using a similar method to that disclosed in WO 2006/015828; the initial solvent for conversion of (S)-5-bromo-2-aminoindane camphorsulfonate salt into the free base form was DCM.

Description 2: N-[(2S)-5-(4,4,5,5-tetramethyl-1,3,2-dioxaborolan-2-yl)-2,3-dihydro-1H-inden-2-yl]-2-propanesulfonamide

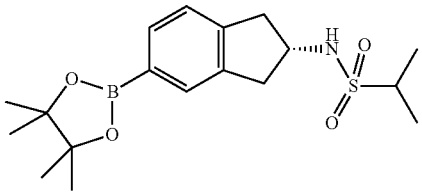

In a 2 L round-bottomed flask at room temperature under argon, N-[(2S)-5-bromo-2,3-dihydro-1H-inden-2-yl]-2-propanesulfonamide (30 g, 94 mmol, Description 1), bis(pinacolato)diboron (35.9 g, 141 mmol) and potassium acetate (27.8 g, 283 mmol) were suspended in dry dimethyl sulfoxide (300 ml). The resulting mixture was degassed with argon for 15 minutes then [1,1'-bis(diphenylphosphino)ferrocene] dichloropalladium (II) (1:1 complex with $CH_2Cl_2$) (3.85 g, 4.71 mmol) was added and the resulting orange suspension was heated at 90° C. internal temperature for 20 hours.

The mixture was cooled down to room temperature, diluted with EtOAc (700 ml) and water (500 ml), then filtered over Sterimat. The filtrate was washed with water (2×400 ml) and brine/water (2:1, 2×400 ml). The collected organic phase was dried over $Na_2SO_4$, filtered and concentrated to give crude material as a brown oil that was purified by flash-chromatography (Biotage 75 L, eluting with cyclohexane/EtOAc=90/10 to 70/30). Evaporation of solvents gave N-[(2S)-5-(4,4,5,5-tetramethyl-1,3,2-dioxaborolan-2-yl)-2,3-dihydro-1H-inden-2-yl]-2-propanesulfonamide (32.4 g) as a pale yellow solid.

UPLC/MS: Found 366 (ES+), retention time 0.79 mins. C$_{18}$H$_{28}$NBO$_4$S requires 365.

Description 3: N-[(2S)-5-hydroxy-2,3-dihydro-1H-inden-2-yl]-2-propanesulfonamide

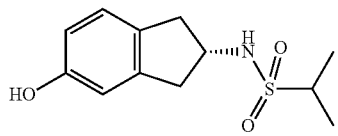

To a solution of N-[(2S)-5-(4,4,5,5-tetramethyl-1,3,2-dioxaborolan-2-yl)-2,3-dihydro-1H-inden-2-yl]-2-propanesulfonamide (32 g, 88 mmol, Description 2) in methanol (320 ml) at room temperature under nitrogen, hydrogen peroxide (30 weight % in water, 17.90 ml, 175 mmol) was added and the resulting pale yellow solution stirred overnight. The mixture was then evaporated under reduced pressure and the residue partitioned between EtOAc (500 ml) and water (300 ml). Aqueous phase was back extracted with EtOAc (300 ml) and the combined organics were washed with brine (100 ml)/water (100 ml), dried over Na$_2$SO$_4$ and evaporated to dryness. The resulting pale yellow solid was triturated with Et$_2$O (100 ml)/n-hexane (100 ml) and dried at high vacuum to give N-[(2S)-5-hydroxy-2,3-dihydro-1H-inden-2-yl]-2-propanesulfonamide (20.85 g) as a pale yellow solid.

UPLC/MS: Found 256 (ES+), retention time 0.54 mins. C$_{12}$H$_{17}$NO$_3$S requires 255.

Description 4: 3-(6-methyl-3-pyridinyl)-1-propanol

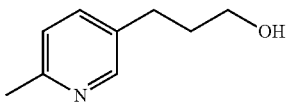

To a suspension of ethyl 3-(6-methyl-3-pyridinyl)propanoate (500 mg, 2.59 mmol) in tetrahydrofuran (15 ml) at 0° C., LiAlH$_4$ (1.42 ml, 2.85 mmol) was added dropwise. When the addition was complete, the ice bath was removed and the reaction stirred at room temperature for 1 hour. Wet THF was added dropwise until a white solid precipitated and the evolution of gas ceased. The solid was filtered off, washed twice with Et$_2$O and the filtrate evaporated under vacuum to afford the title compound (403 mg).

$^1$H NMR (400 MHz, MeOH-d$_4$) δ 1.77-1.88 (m, 2H), 2.48 (s, 3H), 2.67 (t, J=8.0 Hz, 2H), 3.57 (t, J=6.4 Hz, 2H), 7.21 (d, J=8.0 Hz, 1H), 7.59 (dd, J=8.0, 2.3 Hz, 1H), 8.25 (d, J=2.0 Hz, 1H).

Description 5: 1-(6-methyl-3-pyridinyl)ethanol

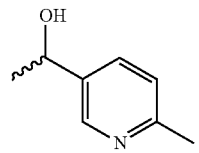

To a stirring solution of 1-(6-methyl-3-pyridinyl)ethanone (1.0 g, 7.4 mmol) in absolute ethanol (10 ml) at 0° C. was added sodium borohydride (0.14 g, 3.7 mmol) portionwise over 20 minutes. The reaction mixture was stirred at 0° C. for 1.5 hours before warming to room temperature. The mixture was partitioned between dichloromethane and saturated aqueous sodium hydrogen carbonate. The organic phase was dried over sodium sulphate, filtered, and evaporated in vacuo to give the crude product 1-(6-methyl-3-pyridinyl)ethanol (810 mg).

$^1$H-NMR (400 MHz, CDCl$_3$): δ 8.45 (1H, s), 7.63 (1H, m), 7.14 (1H, d, J=8 Hz), 4.93 (1H, m), 2.54 (3H, s), 2.09 (1H, bs), 1.53 (3H, m).

Description 6: 5-(chloromethyl)-2-methylpyridine

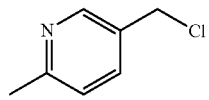

In a 250 ml round-bottomed flask at room temperature under nitrogen, (6-methyl-3-pyridinyl)methanol (4.32 g, 35.1 mmol, D8) was dissolved in dry dichloromethane (45 ml) to give a yellow solution, which was cooled down to 0° C. Thionyl chloride (3 ml, 41.1 mmol) was then added. The resulting pale-orange mixture was stirred at 0° C. for 15 minutes and at room temperature for 2 hours. The mixture was concentrated in vacuum and the brown residue was partitioned between DCM (150 ml) and saturated NaHCO$_3$ (100 ml). Phases were separated and the organic was washed with saturated NaHCO$_3$ (2×100 ml), dried over Na$_2$SO$_4$, filtered and concentrated to give the desired compound as brown oil (4.26 g), that was used without further purification in the next step.

UPLC/MS: Found 141.97, 143.85 (ES+), retention time 0.29 mins. (chlorine pattern) C$_7$H$_8$ClN requires 141 for $^{35}$Cl.

Description 7: 3-(chloromethyl)-2-methylpyridine

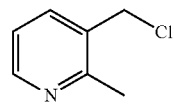

In a 50 ml round bottomed flask, under argon at 0° C., thionyl chloride (12 mL, 164 mmol) was cautiously added to (2-methyl-3-pyridinyl)methanol (8 g, 65.0 mmol). Process was exothermic and white fumes were formed. At the end of the addition the obtained brown solution was heated at 85° C. for 40 minutes. The reaction mixture was evaporated to get the crude material as solid yellow slurry that was then taken up with NaHCO$_3$ saturated solution (300 ml)/DCM (300 ml). The phases were separated and the aqueous one back extracted with DCM (2×200 ml). The combined organics were dried over Na$_2$SO$_4$ and evaporated to dryness to get 3-(chloromethyl)-2-methylpyridine (8.7 g) as a black/brown waxy solid that was used without further purification in the next step.

UPLC/MS: Found 142 (ES+), retention time 0.29 mins. $C_7H_8NCl$ requires 141 for $^{35}Cl$.

Description 8: (6-methyl-3-pyridinyl)methanol

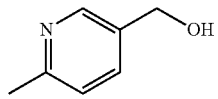

In a 500 ml round-bottomed flask at room temperature under nitrogen, methyl 6-methyl-3-pyridinecarboxylate (10 g, 66.2 mmol) was dissolved in dry tetrahydrofuran (100 ml) to give a orange solution. The mixture was then cooled down to 0° C. and lithium aluminum hydride (36.4 ml, 72.8 mmol) was added dropwise, keeping internal temperature below 0° C. At the end of addition the ice-bath was removed and the resulting solution was stirred at room temperature for 3 hours. The mixture was slowly additioned with 2.73 ml of water, 2.73 ml of NaOH 1M and 8.2 ml of water. The resulting yellow suspension was stirred at room temperature for ~30 minutes and then filtered over a Gooch funnel. The solid was washed with $Et_2O$ (3×100 ml). The combined organics were dried over $Na_2SO_4$, filtered and concentrated to give the title product (7.48 g) as orange oil.

EXAMPLE 1

N-[(2S)-5-(phenyloxy)-2,3-dihydro-1H-inden-2-yl]-2-propanesulfonamide

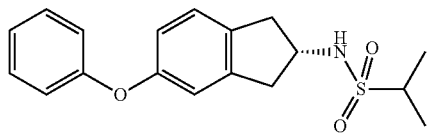

A reaction mixture of N-[(2S)-5-bromo-2,3-dihydro-1H-inden-2-yl]-2-propanesulfonamide (100 mg, 0.31 mmol, Description 1), phenol (30 mg, 0.32 mmol), caesium carbonate (308 mg, 0.94 mmol), copper(I) iodide (66 mg, 0.35 mmol) and N,N-dimethylglycine (39 mg, 0.38 mmol) in DMSO (1.5 ml) was heated in a microwave at 190° C. for 30 minutes. The mixture was quenched with hydrochloric acid (2M) and then partitioned between dichloromethane and water. The organic solution was dried ($MgSO_4$) and evaporated under reduced pressure to yield the crude product. The crude product was purified using MDAP to obtain the title product as a yellow gum (49 mg).

LC/MS (ES): Found 332 (ES+), retention time 3.21 mins. $C_{18}H_{21}NO_3S$ requires 331.

$^1$H NMR (400 MHz, $CDCl_3$): δ 7.33 (2H, m), 7.16 (1H, dd, J=8, 1 Hz), 7.09 (1H, m), 6.99 (2H, m), 6.86 (2H, m), 4.30 (2H, m), 3.29 (2H, m), 3.19 (1H, septet, J=7 Hz), 2.88 (2H, m), 1.40 (6H, d, J=7 Hz).

EXAMPLE 2

N-{(2S)-5-[(2-pyridinylmethyl)oxy]-2,3-dihydro-1H-inden-2-yl}-2-propanesulfonamide

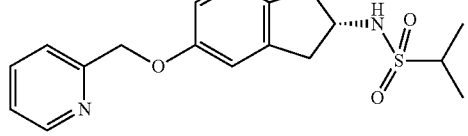

A solution of N-[(2S)-5-hydroxy-2,3-dihydro-1H-inden-2-yl]-2-propanesulfonamide (100 mg, 0.39 mmol, Description 3) and 2-pyridinylmethanol (43 mg, 0.39 mmol) in dichloromethane (3 ml), was treated with triphenylphosphine (103 mg, 0.39 mmol) and then diisopropyl azodicarboxylate (77 ul, 0.39 mmol). The resulting solution was stirred at room temperature, under an atmosphere of argon, for 16 hours. The solution was then partitioned between water and dichloromethane and the organic solution was dried ($MgSO_4$) and evaporated under reduced pressure to yield the crude product. The crude product was purified using MDAP. The resulting solution was diluted with saturated aqueous sodium bicarbonate solution and extracted with dichloromethane. The organic solution was dried ($MgSO_4$) and evaporated under reduced pressure to obtain the title compound as a white solid (70 mg).

LC/MS (ES): Found 347 (ES+), retention time 0.88 mins (2 minute run). $C_{18}H_{22}N_2O_3S$ requires 346.

$^1$H NMR (400 MHz, $CDCl_3$): δ 8.60 (1H, ddd, J=5, 2, 1 Hz), 7.72 (1H, td, J=8, 2 Hz), 7.51 (1H, d, J=8 Hz), 7.23 (1H, m), 7.11 (1H, d, J=8 Hz), 6.85 (1H, m), 6.82 (1H, dd, J=8, 3 Hz), 5.18 (2H, s), 4.28 (2H, m), 3.26 (2H, m), 3.18 (1H, septet, J=7 Hz), 2.85 (2H, m), 1.39 (6H, d, J=7 Hz).

EXAMPLE 3

N-{(2S)-5-[(6-methyl-3-pyridinyl)oxy]-2,3-dihydro-1H-inden-2-yl}-2-propanesulfonamide

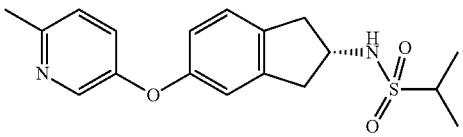

A reaction mixture of N-[(2S)-5-bromo-2,3-dihydro-1H-inden-2-yl]-2-propanesulfonamide (100 mg, 0.31 mmol, Description 1), 6-methyl-3-pyridinol (35 mg, 0.32 mmol), caesium carbonate (308 mg, 0.94 mmol), copper(I) iodide (66 mg, 0.35 mmol) and N,N-dimethylglycine (39 mg, 0.38 mmol) in DMSO (1.5 ml) was heated in a microwave at 190° C. for 30 minutes. The reaction mixture was then partitioned between dichloromethane and water and the organic solution was dried ($MgSO_4$) and evaporated under reduced pressure to yield the crude product. The crude product was purified using MDAP. The resulting solution was diluted with saturated aqueous sodium bicarbonate solution and extracted with dichloromethane. The organic solution was dried (MgSO$_4$) and evaporated under reduced pressure to obtain the title compound as a yellow gum (25 mg).

LC/MS (ES): Found 347 (ES+), retention time 2.00 mins. C$_{18}$H$_{22}$N$_2$O$_3$S requires 346.

$^1$H NMR (400 MHz, CDCl$_3$): δ 8.27 (1H, d, J=3 Hz), 7.20 (1H, dd, J=8, 3 Hz), 7.14 (2H, m), 6.83 (2H, m), 4.31 (2H, m), 3.29 (2H, m), 3.19 (1H, septet, J=7 Hz), 2.88 (2H, m), 2.54 (3H, s), 1.40 (6H, d, J=7 Hz).

EXAMPLE 4

N-[(2S)-5-(2-pyridinyloxy)-2,3-dihydro-1H-inden-2-yl]-2-propanesulfonamide

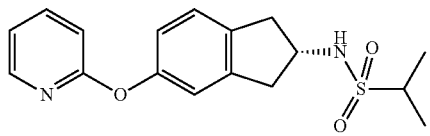

A reaction mixture of N-[(2S)-5-hydroxy-2,3-dihydro-1H-inden-2-yl]-2-propanesulfonamide (100 mg, 0.39 mmol, Description 3), 2-bromopyridine (62 mg, 0.39 mmol), caesium carbonate (382 mg, 1.17 mmol), copper(I) iodide (82 mg, 0.43 mmol) and N,N-dimethylglycine (49 mg, 0.47 mmol) in DMSO (1.5 ml) was heated in a microwave at 190° C. for 30 minutes. The resulting mixture was then partitioned between dichloromethane and water and the organic solution was dried (MgSO$_4$) and evaporated under reduced pressure to yield the crude product. The crude product was purified using MDAP. The resulting solution was diluted with saturated aqueous sodium bicarbonate solution and extracted with dichloromethane. The organic solution was dried (MgSO$_4$) and evaporated under reduced pressure to obtain the title compound as a yellow gum (42 mg).

LC/MS (ES): Found 333 (ES+), retention time 1.01 mins (2 minute run). C$_{17}$H$_{20}$N$_2$O$_3$S requires 332.

$^1$H NMR (400 MHz, CDCl$_3$) δ 8.18 (1H, ddd, J=5, 2, 1 Hz), 7.68 (1H, ddd, J=8, 7, 2 Hz), 7.23 (1H, d, J=8 Hz), 6.96 (4H, m), 4.33 (2H, m), 3.32 (2H, m), 3.19 (1H, septet, J=7 Hz), 2.91 (2H, m), 1.40 (6H, d, J=7 Hz).

EXAMPLE 5

N-{(2S)-5-[(5-fluoro-2-pyridinyl)oxy]-2,3-dihydro-1H-inden-2-yl}-2-propanesulfonamide

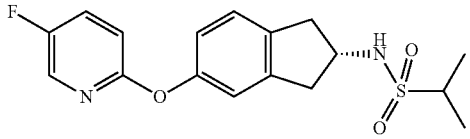

A reaction mixture of N-[(2S)-5-hydroxy-2,3-dihydro-1H-inden-2-yl]-2-propanesulfonamide (100 mg, 0.39 mmol, Description 3), 2-bromo-5-fluoropyridine (69 mg, 0.39 mmol), caesium carbonate (382 mg, 1.17 mmol), copper(I) iodide (82 mg, 0.43 mmol) and N,N-dimethylglycine (49 mg, 0.47 mmol) in DMSO (1.5 ml) was heated in a microwave at 190° C. for 30 minutes. The resulting mixture was then partitioned between dichloromethane and water and the organic solution was dried (MgSO$_4$) and evaporated under reduced pressure to yield the crude product. The crude product was purified using MDAP. The resulting solution was diluted with saturated aqueous sodium bicarbonate solution and extracted with dichloromethane. The organic solution was dried (MgSO$_4$) and evaporated under reduced pressure to obtain the title compound as a pale yellow solid (40 mg).

LC/MS (ES): Found 351 (ES+), retention time 2.83 mins. C$_{17}$H$_{19}$FN$_2$O$_3$S requires 350.

$^1$H NMR (400 MHz, CDCl$_3$): δ 8.01 (1H, d, J=3 Hz), 7.44 (1H, ddd, J=9, 7, 3 Hz), 7.23 (1H, d, J=8 Hz), 6.93 (3H, m), 4.32 (2H, m), 3.32 (2H, m), 3.19 (1H, septet, J=7 Hz), 2.91 (2H, m), 1.40 (6H, d, J=7 Hz).

EXAMPLE 6

N-{(2S)-5-[(2-methyl-3-pyridinyl)oxy]-2,3-dihydro-1H-inden-2-yl}-2-propanesulfonamide, hydrochloride

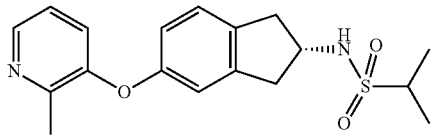

Step 1:

A mixture of 2-methyl-3-pyridinol (8.57 g, 79 mmol), cesium carbonate (51.2 g, 157 mmol) and copper (I) oxide (11.24 g, 79 mmol) in dimethyl sulfoxide (250 mL) was stirred for 5 minutes at room temperature. N-[(2S)-5-bromo-2,3-dihydro-1H-inden-2-yl]-2-propanesulfonamide (25 g, 79 mmol, Description 1) was added followed by N,N-dimethylglycine (8.10 g, 79 mmol). The reaction was heated at 130° C. overnight. The reaction was allowed to reach room temperature and diluted with ethyl acetate (500 ml) then filtered through celite washing with ethyl acetate. The organic phase was washed with water (2×500 ml), dried over Na$_2$SO$_4$ and concentrated in vacuo. This material was purified using Biotage 75 L eluting with cyclohexane/ethyl acetate 2/8 to give N-{(2S)-5-[(2-methyl-3-pyridinyl)oxy]-2,3-dihydro-1H-inden-2-yl}-2-propanesulfonamide (free base, 18.5 g).

UPLC/MS: Found 347 (ES+), retention time 0.52 mins. C$_{18}$H$_{22}$N$_2$O$_3$S requires 346.

Step 2:

N-{(2S)-5-[(2-methyl-3-pyridinyl)oxy]-2,3-dihydro-1H-inden-2-yl}-2-propanesulfonamide (free base, 7.08 g, 20.44 mmol) was dissolved in methanol (150 mL) and dichloromethane (75 mL). HCl (1M in ether, 21.46 mL, 21.46 mmol) was added dropwise at 0° C. and the mixture was stirred at room temperature for 20 minutes. Solvent was removed under reduced pressure to obtain the title compound (7.9 g) containing a minor amount of methanol. 1 g of this material was dried under reduced pressure at 60° C. for 60 hours to give 0.98 g of the title compound.

UPLC/MS: Found 347 (ES+), retention time 0.9 mins. C$_{18}$H$_{22}$N$_2$O$_3$S requires 346.

$^1$H NMR (500 MHz, DMSO-d$_6$): δ 8.46 (1H, d, J=4.9 Hz), 7.70 (2H, m), 7.48 (1H, d, J=7.8 Hz), 7.27 (1H, d, J=7.8 Hz), 7.0 (1H, s), 6.93 (1H, dd, J=8.1, 2.2 Hz), 4.11 (1H, m), 3.19 (3H, m), 2.85 (2H, m), 2.66 (3H, s), 1.24 (6H, d, J=6.4 Hz).

EXAMPLE 7

N-((2S)-5-{[(2-methyl-3-pyridinyl)methyl]oxy}-2,3-dihydro-1H-inden-2-yl)-2-propanesulfonamide, hydrochloride

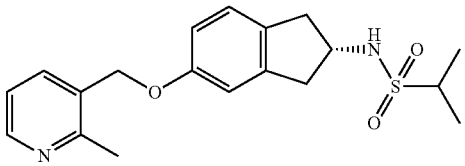

Step 1:

To a solution of N-[(2S)-5-hydroxy-2,3-dihydro-1H-inden-2-yl]-2-propanesulfonamide (1 g, 3.92 mmol, Description 3) in dry N,N-dimethylformamide (4 mL) under argon, cesium carbonate (1.531 g, 4.70 mmol) was added followed by potassium iodide (0.130 g, 0.783 mmol). To the mixture 3-(chloromethyl)-2-methylpyridine (0.665 g, 4.70 mmol, Description 7) dissolved in dry N,N-Dimethylformamide (1 mL) was added and the resulting slurry was stirred at room temperature overnight to give batch 1.

To a solution of N-[(2S)-5-hydroxy-2,3-dihydro-1H-inden-2-yl]-2-propanesulfonamide (8 g, 31.3 mmol, Description 3) in dry N,N-Dimethylformamide (30 mL) under argon, cesium carbonate (12.25 g, 37.6 mmol) was added followed by potassium iodide (1.040 g, 6.27 mmol). To the mixture 3-(chloromethyl)-2-methylpyridine (5.32 g, 37.6 mmol, Description 7) dissolved in dry N,N-Dimethylformamide (10 mL) was added and the resulting slurry was stirred at room temperature overnight to give batch 2. Batches 1 and 2 were combined.

This mixture was chilled at 0° C. and was diluted with water (200 ml) and Et$_2$O (300 ml) (exothermic reaction). EtOAc (200 ml) was added and the mixture was filtered over Celite. Phases were separated and the aqueous one back extracted with EtOAc (2×200 ml) and DCM (2×200 ml). The combined organic phases were washed with brine/water 1/1 (3×100 ml), dried over Na$_2$SO$_4$ and evaporated to dryness. This crude material was purified using a SiO$_2$ column eluting with cyclohexane/EtOAc from 1/1 to 2/8. Evaporation of the solvent afforded N-((2S)-5-{[(2-methyl-3-pyridinyl)methyl]oxy}-2,3-dihydro-1H-inden-2-yl)-2-propanesulfonamide (free base, 10.9 g) as a pale brown foam.

UPLC/MS: Found 361 (ES+), retention time 0.49 mins. C$_{19}$H$_{24}$N$_2$O$_3$S requires 360.

Step 2:

To a solution of N-((2S)-5-{[(2-methyl-3-pyridinyl)methyl]oxy}-2,3-dihydro-1H-inden-2-yl)-2-propanesulfonamide (free base, 6.5 g, 18.03 mmol) in dry methanol (65 mL) at 0° C. under argon, hydrochloric acid (1M in Et$_2$O, 21.64 mL, 21.64 mmol) was added dropwise. The mixture was stirred at 0° C. for 10 minutes then at room temperature for 30 minutes. Volatiles were evaporated under reduced pressure and the resulting solid residue was triturated with Et$_2$O/pentane 40 ml/30 ml. The product was collected by filtration washing the cake with pentane (30 ml) and drying the material at high vacuum to get the title compound (6.95 g) as a white solid.

UPLC/MS: Found 361 (ES+), retention time 0.49 mins. C$_{19}$H$_{24}$N$_2$O$_3$S requires 360.

$^1$H NMR (500 MHz, CDCl$_3$): δ 8.70 (1H, d, J=5.4 Hz), 8.43 (1H, m), 7.83 (1H, m), 7.43 (1H, d, J=7.8 Hz), 7.13 (1H, d, J=8.3 Hz), 6.96 (1H, s), 6.88 (1H, dd, J=2.2, 8.2 Hz), 5.24 (2H, s), 4.08 (1H, m), 3.21 (1H, m), 3.12 (2H, m), 2.82 (2H, m), 2.74 (3H, s), 1.25 (6H, d, J=6.7 Hz).

EXAMPLE 8

N-{(2S)-5-[(4-methyl-3-pyridinyl)oxy]-2,3-dihydro-1H-inden-2-yl}-2-propanesulfonamide, hydrochloride

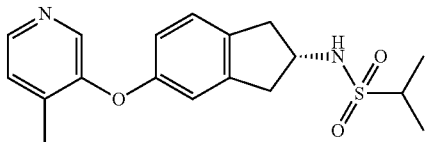

A mixture of 4-methyl-3-pyridinol (71.1 mg, 0.652 mmol), N-[(2S)-5-bromo-2,3-dihydro-1H-inden-2-yl]-2-propanesulfonamide (200 mg, 0.628 mmol, Description 1), N,N-dimethylglycine (78 mg, 0.754 mmol), caesium carbonate (410 mg, 1.257 mmol) and copper(I) iodide (132 mg, 0.691 mmol) in DMSO (2 ml) was heated under microwave conditions at 190° C. for 30 minutes. The mixture was filtered through kieselguhr and partitioned between ethyl acetate and water. The organic solution was dried and evaporated under reduced pressure to yield the crude product. This material was purified using MDAP and then partitioned between ethyl acetate and saturated aqueous sodium bicarbonate solution. The organic layer was dried (Na$_2$SO$_4$) and evaporated under reduced pressure. The resulting free base was treated with 1 ml of ethereal HCl and the ether was evaporated to yield the desired product as an orange gum (30 mg).

LC/MS (ES): Found 347 (ES+), retention time 2.01 mins. C$_{18}$H$_{22}$N$_2$O$_3$S requires 346.

$^1$H NMR free base (400 MHz, DMSO-d$_6$): δ 8.28 (1H, d, J=5 Hz), 8.11 (1H, s), 7.45 (1H, d, J=8 Hz), 7.37 (1H, d, J=5 Hz), 7.18 (1H, d, J=8 Hz), 6.78 (1H, d, J=2 Hz), 6.73 (1H, dd, J=8, 2 Hz), 4.09 (1H, m), 3.21 (1H, septet, J=7 Hz), 3.14 (2H, m), 2.81 (2H, m), 2.20 (3H, s), 1.24 (6H, d, J=7 Hz).

EXAMPLE 9

N-((2S)-5-{[(6-methyl-3-pyridinyl)methyl]oxy}-2,3-dihydro-1H-inden-2-yl)-2-propanesulfonamide, hydrochloride

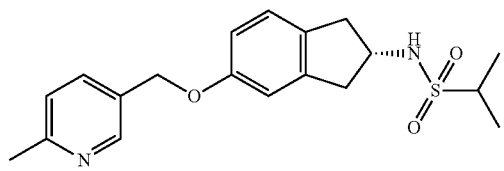

Step 1:

In a 250 ml round-bottomed flask at room temperature under nitrogen, N-[(2S)-5-hydroxy-2,3-dihydro-1H-inden-2-yl]-2-propanesulfonamide (5.31 g, 20.80 mmol, Description 3) was dissolved in N,N-dimethylformamide (25 ml) to give a colourless solution. Cesium carbonate (10.16 g, 31.2 mmol) was then added, followed by 5-(chloromethyl)-2-methylpyridine (4.26 g, 30.1 mmol, Description 6) dissolved in dry N,N-dimethylformamide (20 ml), and potassium iodide (0.863 g, 5.20 mmol). This resulting brown mixture was then allowed to stir at room temperature for the weekend. The mixture was brought to 0° C. and was diluted with water (100 ml) and DCM (150 ml) (exothermic reaction). Phases were separated and the aqueous phase was back extracted with DCM (2×100 ml). The combined organic phases were dried over $Na_2SO_4$, filtered and concentrated to give an oily residue, which was diluted in $Et_2O$ (250 ml) and washed with water (2×100 ml). The organic was dried again over $Na_2SO_4$, filtered and concentrated to give 8.8 g as a brown foam, which was purified by flash-chromatography (100 g $SiO_2$ cartridge, eluting with cyclohexane/EtOAc=60/40, 1/1 and 40/60) to give N-((2S)-5-{[(6-methyl-3-pyridinyl)methyl]oxy}-2,3-dihydro-1H-inden-2-yl)-2-propanesulfonamide (free base) as a pale-yellow solid (3.43 g).

UPLC/MS: Found 361 (ES+), retention time 0.50 mins. $C_{19}H_{24}N_2O_3S$ requires 360.

Step 2:

In a 250 ml round-bottomed flask at room temperature under nitrogen, N-((2S)-5-{[(6-methyl-3-pyridinyl)methyl]oxy}-2,3-dihydro-1H-inden-2-yl)-2-propanesulfonamide (free base, 5.03 g, 13.95 mmol) was dissolved in dry methanol (60 ml) to give a yellow solution, which was then cooled down to 0° C. Hydrochloric acid (1M in $Et_2O$, 14 ml, 14.00 mmol) was then added dropwise and the resulting yellow solution was stirred at 0° C. for 30 minutes and at room temperature for 1 hour: after few minutes at 0° C. a white solid appeared, which dissolved almost completely at room temperature.

The mixture was then evaporated under vacuum and stripped with dry $Et_2O$ (25 ml) to obtain a pale-yellow solid. This material was suspended in dry n-pentane (25 ml) and allowed to stir at room temperature under nitrogen for 1 hour. Then the solid was filtered off over a Gooch funnel, collected and kept under high vacuum overnight to give the desired compound as an off-white solid (4.93 g).

UPLC/MS: Found 361 (ES+), retention time 0.49 mins. $C_{19}H_{24}N_2O_3S$ requires 360.

1H NMR (500 MHz, DMSO-$d_6$) δ 8.78 (s, 1H), 8.39 (d, J=8.0 Hz, 1H), 7.82 (d, J=8.2 Hz, 1H), 7.39 (d, J=7.6 Hz, 1H), 7.09 (d, J=8.2 Hz, 1H), 6.89 (s, 1H), 6.78 (d, J=8.2 Hz, 1H), 5.20 (s, 2H), 3.97-4.12 (m, 1H), 3.15-3.25 (m, 1H), 3.01-3.15 (m, 2H), 2.70-2.85 (m, 2H), 2.69 (s, 3H), 1.23 (d, J=6.7 Hz, 6H).

Alternatively:

A mixture of N-[(2S)-5-hydroxy-2,3-dihydro-1H-inden-2-yl]-2-propanesulfonamide (700 mg, 2.74 mmol, Description 3) and (6-methyl-3-pyridinyl)methanol (338 mg, 2.74 mmol) in dichloromethane (30 ml) was stirred under argon at room temperature, Triphenylphosphine (719 mg, 2.74 mmol) and diisopropyl azodicarboxylate (0.533 ml, 2.74 mmol) were then successively added. The resulting mixture was stirred at room temperature under argon for 16 hours. The reaction mixture was washed with water, dried over sodium sulphate, filtered and evaporated. The desired product was purified by SCX column eluting with 1 M ammonia in methanol solution and column chromatography on silica using 1 to 99% ethyl acetate in n-pentane to give a white solid. The free base solid was dissolved in methanol and treated with ethereal hydrochloride to give the title compound (554 mg).

EXAMPLE 10

N-{(2S)-5-[(3-pyridinylmethyl)oxy]-2,3-dihydro-1H-inden-2-yl}-2-propanesulfonamide, hydrochloride

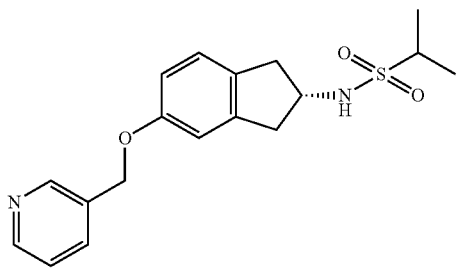

A mixture of N-[(2S)-5-hydroxy-2,3-dihydro-1H-inden-2-yl]-2-propanesulfonamide (120 mg, 0.470 mmol, Description 3) and 3-pyridinylmethanol (51.3 mg, 0.470 mmol) in dichloromethane (10 ml) was stirred under argon at room temperature. Triphenylphosphine (123 mg, 0.470 mmol) and diisopropyl azodicarboxylate (0.091 ml, 0.470 mmol) were then successively added. The resulting mixture was stirred at room temperature under argon for 16 hours. The reaction mixture was washed with water, dried over sodium sulphate, filtered and evaporated. The desired product was purified by column chromatography on silica eluting with 1 to 99% ethyl acetate in n-pentane and then by SCX column eluting with 1M ammonia in methanol solution to give the title compound as a white solid. The free base solid was dissolved in methanol and treated with ethereal hydrochloride to give the HCl salt (64 mg).

LC/MS (ES): Found 347 (ES+), retention time 1.94 mins. $C_{18}H_{22}N_2O_3S$ requires 346.

1H NMR (400 MHz, DMSO-$d_6$): δ 8.89 (1H, d, J=1 Hz), 8.79 (1H, dd, J=5, 1 Hz), 8.38 (1H, d, J=8 Hz), 7.88 (1H, dd, J=8, 5 Hz), 7.44 (1H, d, J=8 Hz), 7.12 (1H, d, J=8 Hz), 6.91 (1H, d, J=2 Hz), 6.83 (1H, dd, J=8, 2 Hz), 5.24 (2H, s), 4.07 (1H, sextet, J=8 Hz), 3.22 (1H, septet, J=7 Hz), 3.12 (2H, m), 2.80 (2H, m), 1.24 (6H, d, J=7 Hz).

EXAMPLE 11

N-((2S)-5-{[3-(3-pyridinyl)propyl]oxy}-2,3-dihydro-1H-inden-2-yl)-2-propanesulfonamide

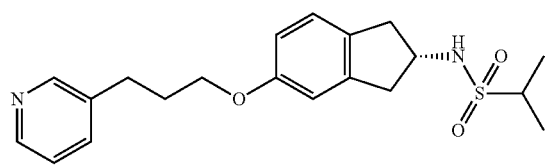

To a solution of N-[(2S)-5-hydroxy-2,3-dihydro-1H-inden-2-yl]-2-propanesulfonamide (50 mg, 0.196 mmol, Description 3) and 3-pyridinepropanol (0.028 ml, 0.215 mmol) in dichloromethane (1 ml) was added diisopropyl azodicarboxylate (0.038 ml, 0.196 mmol) followed by triphenylphosphine (51.4 mg, 0.196 mmol). The reaction mixture was stirred at 25° C. overnight. Solvent was removed under vacuum and the crude product was purified by reverse phase chromatography using the MDAP. Relevant fractions were combined and concentrated to give 34 mg of material which was dried in the vacuum oven overnight. This solid was then dissolved in DCM (10 ml) and washed with water (2*10 ml). The organic phase was dried over $MgSO_4$ and concentrated. This product was purified by MDAP a second time. This material was dissolved in MeOH and loaded on to a SCX cartridge, washed with MeOH and eluted with methanolic ammonia. Relevant fractions were combined and concentrated to give the title compound as a white solid (2 mg).

LC/MS (ES): Found 375 (ES+), retention time 0.68 mins (2 minute method). $C_{20}H_{26}N_2O_3S$ requires 374.

$^1$H NMR (400 MHz, MeOH-$d_4$): δ 8.38 (2H, m), 7.72 (1H, m), 7.36 (1H, m), 7.06 (1H, m), 6.76 (1H, m), 6.69 (1H, m), 4.16 (1H, m), 3.93 (2H, t, J=6 Hz), 3.18 (3H, m), 2.81 (4H, m), 2.05 (2H, m), 1.35 (6H, d, J=6.8 Hz).

EXAMPLE 12

N-((2S)-5-{[3-(6-methyl-3-pyridinyl)propyl]oxy}-2,3-dihydro-1H-inden-2-yl)-2-propanesulfonamide, hydrochloride

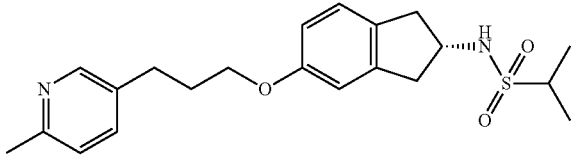

To a solution of N-[(2S)-5-hydroxy-2,3-dihydro-1H-inden-2-yl]-2-propanesulfonamide (200 mg, 0.783 mmol, Description 3) and 3-(6-methyl-3-pyridinyl)-1-propanol (178 mg, 1.175 mmol, Description 4) in dichloromethane (4 ml) was added diisopropyl azodicarboxylate (0.183 ml, 0.940 mmol) followed by triphenylphosphine (247 mg, 0.940 mmol). The reaction mixture was shaken at 25° C. overnight. and then stirred at room temperature for a further 2 days. Solvent was removed; residue was dissolved in MeOH and loaded onto an SCX cartridge conditioned with MeOH. Product was washed with MeOH and eluted with methanolic ammonia. Relevant fractions were concentrated to give 200 mg of a yellow solid which was purified using the MDAP. Relevant fractions were combined and concentrated to give 55 mg of a clear oil which was dissolved in 2 ml of DCM and 0.27 ml of 1M HCl in ether was added. The mixture was stirred at room temperature for 5 minutes and then solvent was removed to afford the title compound as a white solid (60 mg).

LC/MS (ES): Found 389 (ES+), retention time 0.70 mins (2 minute method). $O_{21}H_{28}N_2O_3S$ requires 388.

1H NMR (400 MHz, MeOH-$d_4$): δ 1.35 (d, J=6.7 Hz, 6H), 2.16 (m, 2H), 2.76 (s, 3H), 2.78-2.92 (m, 2H), 3.03 (t, J=7.4 Hz, 2H), 3.10-3.28 (m, 3H), 3.99 (t, J=5.7 Hz, 2H), 4.15 (quintet, J=7.5 Hz, 1H), 6.68 (d, J=8.1 Hz, 1H), 6.74 (s, 1H), 7.06 (d, J=8.2 Hz, 1H), 7.85 (d, J=8.1 Hz, 1H), 8.41 (d, J=8.0 Hz, 1H), 8.60 (s, 1H).

EXAMPLE 13

N-{(2S)-5-[(6-methyl-2-pyridinyl)oxy]-2,3-dihydro-1H-inden-2-yl}-2-propanesulfonamide

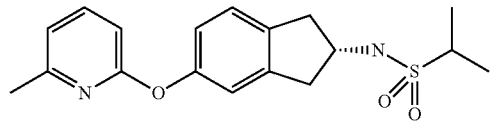

N-[(2S)-5-hydroxy-2,3-dihydro-1H-inden-2-yl]-2-propanesulfonamide (50 mg, 0.196 mmol, Description 3), copper(I) iodide (41.0 mg, 0.215 mmol), 2-bromo-6-methylpyridine (0.022 ml, 0.196 mmol), $Cs_2CO_3$ (191 mg, 0.587 mmol) and N,N-dimethylglycine (24.23 mg, 0.235 mmol), in dimethyl sulfoxide (2 ml) were heated under microwave conditions for 30 minutes at 190° C. The reaction mixture was partitioned between EtOAc (10 ml) and water (5 ml). The organic solution was dried ($Na_2SO_4$) and evaporated under reduced pressure to yield the impure product as a dark brown oil. The product was purified by reverse phase chromatography using the MDAP to afford the title compound as a white solid (17 mg).

LC/MS (ES): Found 347 (ES+), retention time 1.02 mins (2 minute method). $C_{18}H_{22}N_2O_3S$ requires 346.

1H NMR (400 MHz, MeOH-$d_4$) δ 1.36 (d, J=6.8 Hz, 6H), 2.41 (s, 3H), 2.84-2.98 (m, 2H), 3.19-3.28 (m, 3H), 4.23 (quintet, J=8.4 Hz, 1H), 6.57 (d, J=8.4 Hz, 1H), 6.87 (dd, J=8.2, 2.2 Hz, 1H), 6.92-7.00 (m, 2H), 7.23 (d, J=8.0 Hz, 1H), 7.65 (t, J=7.4 Hz, 1H).

EXAMPLE 14

N-{(2S)-5-[(5-methyl-2-pyridinyl)oxy]-2,3-dihydro-1H-inden-2-yl}-2-propanesulfonamide

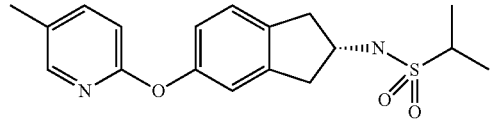

N-[(2S)-5-hydroxy-2,3-dihydro-1H-inden-2-yl]-2-propanesulfonamide (50 mg, 0.196 mmol, Description 3), copper(I) iodide (41.0 mg, 0.215 mmol), 2-bromo-5-methylpyridine (33.7 mg, 0.196 mmol), $Cs_2CO_3$ (191 mg, 0.587 mmol) and N,N-dimethylglycine (24.23 mg, 0.235 mmol), in dimethyl sulfoxide (2 ml) were heated under microwave conditions for 30 minutes at 190° C. The reaction mixture was partitioned between EtOAc (10 ml) and water (5 ml). Aqueous was further extracted with DCM (10 ml). The organic solution was dried ($Na_2SO_4$) and evaporated under reduced pressure to yield the impure product as a dark brown oil. The product was purified by reverse phase chromatography using MDAP to give the title compound as a solid (17 mg).

LC/MS (ES): Found 347 (ES+), retention time 1.04 mins (2 minute method). $C_{18}H_{22}N_2O_3S$ requires 346.

1H NMR (400 MHz, MeOH-d$_4$) δ 1.35 (d, J=6.9 Hz, 6H), 2.28 (s, 3H), 2.85-2.96 (m, 2H), 3.18-3.29 (m, 3H), 4.22 (quintet, J=7.4 Hz, 1H), 6.79 (d, J=8.4 Hz, 1H), 6.85 (dd, J=8.0, 2.4 Hz, 1H), 6.91 (d, J=1.9 Hz, 1H), 7.21 (d, J=8.2 Hz, 1H), 7.60-7.66 (m, 1H), 7.93 (dd, J=1.7, 0.8 Hz, 1H).

EXAMPLE 15

N-{(2S)-5-[(4-methyl-2-pyridinyl)oxy]-2,3-dihydro-1H-inden-2-yl}-2-propanesulfonamide

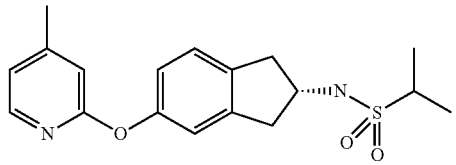

N-[(2S)-5-hydroxy-2,3-dihydro-1H-inden-2-yl]-2-propanesulfonamide (50 mg, 0.196 mmol, Description 3), copper(I) iodide (41.0 mg, 0.215 mmol), 2-bromo-4-methylpyridine (0.022 ml, 0.196 mmol), Cs$_2$CO$_3$ (191 mg, 0.587 mmol) and N,N-dimethylglycine (24.23 mg, 0.235 mmol) in dimethyl sulfoxide (2 ml) were heated under microwave conditions for 30 minutes at 190° C. The reaction mixture was partitioned between EtOAc (10 ml) and water (10 ml). Aqueous was further extracted with DCM (10 ml). The organic solution was dried over MgSO$_4$ and evaporated under reduced pressure to yield the impure product as a dark brown oil. The product was purified by reverse phase chromatography using the MDAP to give the title compound as a white solid (5 mg).

LC/MS (ES): Found 347 (ES+), retention time 1.03 mins (2 minute method). C$_{18}$H$_{22}$N$_2$O$_3$S requires 346.

1H NMR (400 MHz, MeOH-d$_4$) δ 1.36 (d, J=6.9 Hz, 6H), 2.33 (s, 3H), 2.86-2.96 (m, 2H), 3.20-3.29 (m, 3H), 4.23 (quintet, J=7.4 Hz, 1H), 6.71 (s, 1H), 6.86 (dd, J=8.0, 2.4 Hz, 1H), 6.91-6.98 (m, 2H), 7.23 (d, J=8.1 Hz, 1H), 7.96 (d, J=5.3 Hz, 1H).

EXAMPLE 16

N-((2S)-5-{[2-(3-pyridinyl)ethyl]oxy}-2,3-dihydro-1H-inden-2-yl)-2-propanesulfonamide

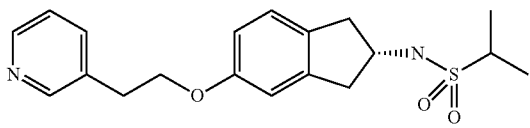

N-[(2S)-5-hydroxy-2,3-dihydro-1H-inden-2-yl]-2-propanesulfonamide (50 mg, 0.196 mmol, Description 3) was dissolved in dichloromethane (1 ml), and triphenylphosphine (51.4 mg, 0.196 mmol) and DIAD (0.038 ml, 0.196 mmol) were added to the reaction mixture. 3-(2-hydroethyl)pyridine was added and reaction mixture was stirred at 25° C. overnight. Solvent was then removed under vacuum and the crude product was purified by reverse phase chromatography using the MDAP. Relevant fractions were combined and concentrated. The residue was dissolved in MeOH and loaded on to a SCX cartridge. The SCX cartridge was eluted with methanol. Product was eluted with methanolic ammonia. Relevant fractions were concentrated and the product was dried in the vacuum oven for 72 hours to obtain the title compound (23 mg).

LC/MS (ES): Found 361 (ES+), retention time 0.63 mins (2 minute method). C$_{19}$H$_{24}$N$_2$O$_3$S requires 360.

$^1$H NMR (400 MHz, MeOH-d$_4$) δ 1.34 (d, J=6.8 Hz, 6H), 2.74-2.89 (m, 2H), 3.01-3.27 (m, 5H), 4.01-4.28 (m, 3H), 6.68 (dd, J=8.3, 2.4 Hz, 1H), 6.75 (d, J=1.9 Hz, 1H), 7.04 (d, J=8.3 Hz, 1H), 7.40 (ddd, J=7.8, 5.0, 0.6 Hz, 1H), 7.80-7.96 (m, 1H), 8.40 (dd, J=5.0, 1.5 Hz, 1H), 8.50 (d, J=1.7 Hz, 1H).

EXAMPLE 17

N-((2S)-5-{[(2,6-dimethyl-3-pyridinyl)methyl]oxy}-2,3-dihydro-1H-inden-2-yl)-2-propanesulfonamide, hydrochloride

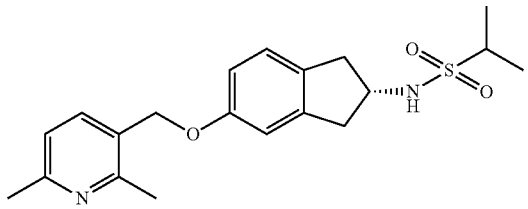

A mixture of N-[(2S)-5-hydroxy-2,3-dihydro-1H-inden-2-yl]-2-propanesulfonamide (149 mg, 0.583 mmol, Description 3) and (2,6-dimethyl-3-pyridinyl)methanol (80 mg, 0.583 mmol) in dichloromethane (10 ml) was stirred under argon at room temperature. Triphenylphosphine (153 mg, 0.583 mmol) and DIAD (0.113 ml, 0.583 mmol) were then successively added. The resulting mixture was stirred at room temperature under argon for 16 hours. Then the reaction mixture was washed with water, dried over sodium sulphate, filtered and evaporated. The desired product was isolated by MDAP, concentrated to a small volume, and partitioned between dichloromethane and aqueous sodium hydrogen carbonate solution. The organic phase was dried over sodium sulphate, filtered and evaporated in vacuo to afford the desired compound as a free base. This was treated with ethereal hydrochloride/methanol to give the title compound as a white solid (92 mg).

LC/MS (ES): Found 375 (ES+), retention time 1.67 mins. C$_{20}$H$_{26}$N$_2$O$_3$S requires 374.

$^1$H-NMR (400 MHz, DMSO-d$_6$): δ 8.34 (1H, bs), 7.69 (1H, bs), 7.46 (1H, d, J=8.0 Hz), 7.14 (1H, d, J=8.0 Hz), 6.94

(1H, s), 6.84 (1H, m), 5.19 (2H, s), 4.06 (1H, m), 3.24-3.06 (3H, m), 2.87-2.74 (2H, m), 2.69 (3H, s), 2.60 (3H, s), 1.25 (6H, d, J=6.8 Hz).

EXAMPLE 18

N-{(2S)-5-[(4-pyridinylmethyl)oxy]-2,3-dihydro-1H-inden-2-yl}-2-propanesulfonamide, hydrochloride

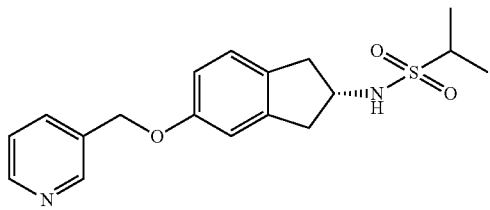

A mixture of N-[(2S)-5-hydroxy-2,3-dihydro-1H-inden-2-yl]-2-propanesulfonamide (100 mg, 0.392 mmol, Description 3) and 4-pyridinylmethanol (42.7 mg, 0.392 mmol) in DCM (10 ml) were stirred under argon at room temperature. Triphenylphosphine (103 mg, 0.392 mmol) and diisopropyl azodicarboxylate (0.076 ml, 0.392 mmol) were then successively added. The resulting mixture was stirred at room temperature under argon for 16 hours. The reaction mixture was washed with water, dried over sodium sulphate, filtered and evaporated. The desired product was isolated by MDAP and concentrated to a small volume. The residual material was partitioned between dichloromethane and aqueous sodium bicarbonate solution, then the organic layer was separated and evaporated. The free base was dissolved in methanol and treated with ethereal hydrochloride to give the title compound as a hydrochloride salt (84 mg).

LC/MS (ES): Found 347 (ES+), retention time 1.75 mins. $C_{18}H_{22}N_2O_3S$ requires 346.

$^1$H-NMR (400 MHz, DMSO-$d_6$): δ 8.86 (2H, d, J=6.4 Hz), 7.94 (2H, d, J=6.4 Hz), 7.44 (1H, d, J=7.6 Hz), 7.13 (1H, d, J=8.0 Hz), 6.93 (1H, d, J=2.0 Hz), 6.82 (1H, m), 5.39 (2H, s), 4.08 (1H, m), 3.22 (1H, m), 3.19-3.04 (2H, m), 2.85-2.75 (2H, m), 1.26 (6H, d, J=6.8 Hz).

EXAMPLE 19

N-((2S)-5-{[(2-methyl-4-pyridinyl)methyl]oxy}-2,3-dihydro-1H-inden-2-yl)-2-propanesulfonamide, hydrochloride

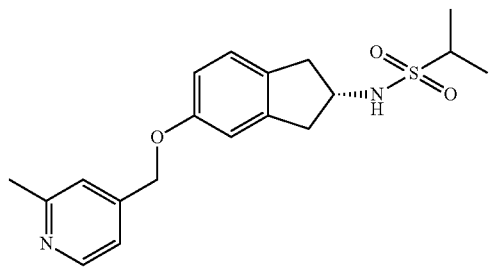

A mixture of N-[(2S)-5-hydroxy-2,3-dihydro-1H-inden-2-yl]-2-propanesulfonamide (200 mg, 0.783 mmol, Description 3) and (2-methyl-4-pyridinyl)methanol (107 mg, 0.783 mmol) in dichloromethane (15 ml) was stirred under argon at room temperature, Triphenylphosphine (205 mg, 0.783 mmol) and diisopropyl azodicarboxylate (0.152 ml, 0.783 mmol) were then successively added. The resulting mixture was stirred at room temperature under argon for 16 hours. Solvent was removed by rotary evaporation and the desired product was purified by SCX eluting with 1M ammonia in methanol solution and high pH MDAP to give the title compound as a white solid. The free base solid was dissolved in methanol and treated with ethereal hydrochloride to give the desired compound as a hydrochloride salt (54 mg).

LC/MS (ES): Found 361 (ES+), retention time 2.77 mins (high pH method). $C_{19}H_{24}N_2O_3S$ requires 360.

$^1$H-NMR (400 MHz, DMSO-$d_6$): δ 8.74 (1H, d, J=6 Hz), 7.89 (1H, s), 7.80 (1H, d, J=6 Hz), 7.45 (1H, d, J=7.6 Hz), 7.12 (1H, d, J=8.4 Hz), 6.90 (1H, d, J=2.4 Hz), 6.83 (1H, m), 5.36 (2H, s), 4.07 (1H, m), 3.34-3.03 (3H, m), 2.87-2.73 (2H, m), 2.75 (3H, s), 1.26 (6H, d, J=6.8 Hz).

EXAMPLE 20

N-((2 S)-5-{[(1S)-1-(6-methyl-3-pyridinyl)ethyl]oxy}-2,3-dihydro-1H-inden-2-yl)-2-propanesulfonamide, hydrochloride and N-((2S)-5-{[(1R)-1-(6-methyl-3-pyridinyl)ethyl]oxy}-2,3-dihydro-1H-inden-2-yl)-2-propanesulfonamide, hydrochloride

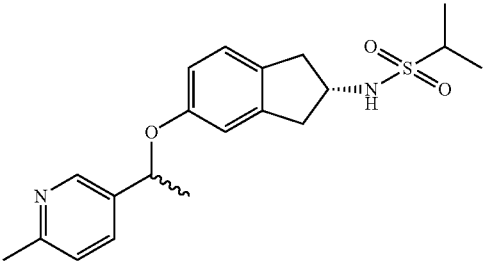

A mixture of N-[(2S)-5-hydroxy-2,3-dihydro-1H-inden-2-yl]-2-propanesulfonamide (200 mg, 0.783 mmol, Description 3) and 1-(6-methyl-3-pyridinyl)ethanol (107 mg, 0.783 mmol, Description 5) in dichloromethane (10 ml) was stirred under argon at room temperature, Triphenylphosphine (205 mg, 0.783 mmol) and diisopropyl azodicarboxylate (0.152 ml, 0.783 mmol) were then successively added. The resulting mixture was stirred at room temperature under argon for 16 hours. Solvent was removed by rotary evaporation and the desired product was purified by SCX eluting with 1M ammonia in methanol solution and MDAP, then concentrated to a small volume. The residual material was partitioned between dichloromethane and aqueous sodium hydrogen carbonate solution. The organic phase was dried over sodium sulphate, filtered and evaporated in vacuo to give the product as free base. The free base was dissolved in methanol and treated with ethereal hydrochloride to give the title compound (121 mg) as a white solid.

LC/MS (ES): Found 375 (ES+), retention time 0.70 mins (2 minute method). $C_{20}H_{26}N_2O_3S$ requires 374.

$^1$H-NMR (400 MHz, DMSO-$d_6$): δ 8.78 (1H, d, J=1.6 Hz), 8.42 (1H, m), 7.84 (1H, d, J=8.4 Hz), 7.40 (1H, m), 7.04 (1H, d, J=8.4 Hz), 6.83 (1H, s), 6.74 (1H, m), 5.69 (1H, m), 4.03 (1H, m), 3.21-3.16 (1H, m), 3.09-3.01 (2H, m), 2.78-2.70 (2H, m), 2.69 (3H, s) 1.58 (3H, d, J=6.4 Hz), 1.22 (6H, d, J=6.8 Hz).

The ability of the compounds of the invention to potentiate AMPA may be determined by the assays below. In the assays used and described herein, the compounds of the present invention were not necessarily from the same batch described above. A test compound from one batch may have been combined with other batch(es) for the assay(s).

Calcium Influx Fluorescence Assay 384 well plates were prepared containing confluent monolayer of HEK 293 cells stably expressing human GluR2 flip (unedited) AMPA receptor subunit. On the day of the experiment, culture medium were discarded and the cells were washed three times with standard buffer (145 mM NaCl, 5 mM KCl, 1 mM $MgCl_2$, 2 mM $CaCl_2$, 20 mM N-[2-hydroxyethyl]-piperazine-N-[2-ethanesulfonic acid (HEPES), 5.5 mM glucose, pH 7.3 with NaOH). 20 µL of buffer remained in each well after washing. The plates were then incubated at room temperature for 60 minutes in the dark with 20 uL/well of FLUO-4 AM buffer (4 uM FLUO-4 AM, pluronic acid F127 0.05%, standard buffer) to allow cell uptake of the FLUO-4 AM, which was then converted to FLUO-4 by intracellular esterases which is unable to leave the cells. After incubation cells were washed three times with buffer. 30 µL of buffer remained in each well after washing. Compounds of the invention were tested in a final assay concentration range from 50 µM to 50 nM. Compounds of the invention (or the reference compound N-[(2R)-2-(4'-cyano-4-biphenylyl)propyl]-2-propanesulfonamide) were dissolved in dimethylsulfoxide (DMSO) at a stock concentration of 10 mM. These solutions were further diluted with DMSO in a 384 compound plate and 1 µL of each dilution was transferred to another compound plate. Just prior to the addition of the compounds to the cells, 50 µL pluronic buffer (standard buffer with 0.05% pluronic-F127 acid) was added to the 1 µL compound copy plate. An agonist stimulus 384-well plate containing 50 µL/well of 500 µM glutamate was prepared by diluting with pluronic buffer (standard buffer with 0.05% pluronic-F127 acid) a 100 mM sodium glutamate stock solution prepared in water. 10 µL from each plate containing a compound of the invention made up in compound buffer solution was added and incubated with the loaded cells for 10 minute in the dark at room temperature. The cell plate was then transferred into a fluorescence imaging plate based reader (such as the FLIPR384—Molecular Devices). A baseline fluorescence reading was taken over a 5 to 10 second period, and then 10 µL of 500 µM glutamate solution was added (to give a final concentration of 100 µM). The fluorescence was then read over a 4-5 minute period. The activities of the compounds of the invention and reference compounds were determined by measuring peak fluorescence after the last addition. The activity was also expressed relative to the fluorescence increase induced by 5 µM N-[(2R)-2-(4'-cyano-4-biphenylyl)propyl]-2-propanesulfonamide at its maximum response. The assay described above is believed to have an effective limit of detection of a $pEC_{50}$ in the region of 3.5-4.0 due to the limitations of compound solubility. The $pEC_{50}$ result is generally considered to be accurate +/−0.3.

All the Example compounds were screened using the assay described above and gave a $pEC_{50}$ equal to or greater than 4.0 and/or demonstrated an activity of on average at least 10% that of N-[(2R)-2-(4'-cyano-4-biphenylyl)propyl]-2-propanesulfonamide (at its maximal response).

Whole Cell Voltage-Clamp Electrophysiology Assay

The ability of the compounds of the invention to potentiate AMPA-subtype glutamate receptor-mediated response may also be determined by measuring AMPA-evoked current recorded from rat cultured hippocampal neurons.

This assay involves the electrophysiological characterisation of AMPA receptor positive modulators using rat cultured hippocampal neurons. The extracellular recording solution contained: 145 mM NaCl, 2.5 mM KCl, 1.2 mM $MgCl_2$, 1.5 mM $CaCl_2$, 10 mM N-[2-hydroxyethyl]-piperazine-N-[2-ethanesulfonic acid (HEPES), 10 mM D-glucose, pH 7.3 with NaOH. The intracellular solution contained: 80 mM CsCl, 80 mM CsF, 10 mM N-[2-hydroxyethyl]-piperazine-N-[2-ethanesulfonic acid (HEPES), 10 mM ethylene glycol-bis(g-aminoethylether)-N,N,N',N,-tetra-acetic acid (EGTA), 14 mM MgATP, 14 mM DiTris Creatine Phosphate, 50 U/ml Creatine Phosphokinase pH 7.3 with CsOH. Recording electrodes were prepared from glass capillary tubes (Clark Electromedical GC120-F10) pulled into two equal lengths using a Zeitz Instruments DMZ Universal Puller, program 09, resulting in electrodes with a resistance of approximately 3-6 MOhms when measured in extracellular solution. Electrodes were back filled with internal recording solution. Positive pressure was applied to the electrode to prevent mixture of internal and external solutions and assist in formation of high resistance seal when the electrode makes contact with the cell membrane. Glass coverslip fragment, bearing rat cultured hippocampal neurons, was placed in the recording chamber positioned on the stage of an inverted microscope. A tube at the edge of the chamber was used to apply extracellular solution to the bath. Rapid solution exchange used a fast step perfusion system (Biologic RSC160). Two outlet tubes attached together along their length were positioned close to a chosen cell so that the outflow from only one tube can pass directly over the cell surface. A motorized stepper could re-position the tubes such that the outflow from the second outlet tube flows over the cell allowing solution exchange at the cell membrane surface to occur within 10-20 ms. Excess bath solution was removed via a tube positioned at the edge of the chamber connected to a vacuum line. A prospective cell was positioned in the centre of the microscope field of view. Recording electrode was positioned directly above the cell membrane surface. Using fine manipulator control (Luigs and Neumann, SM-6) the electrode was lowered, while monitoring the change in electrode resistance during delivery of a 5 mV depolarizing pulse, until a high resistance seal (gigaseal) was achieved. Whole cell configuration was achieved by removing by suction a small fragment of cell membrane immediately beneath the recording electrode tip. The cell membrane potential was held at −70 mV (voltage-clamped) via the electrode (Axopatch 200B Integrating patch clamp amplifier, pClamp software, Axon Instruments). Test solutions were applied using the fast application system using the following protocol and changes in inward current are recorded and stored for off-line analysis.

1) Control current—exchange from extracellular solution to extracellular solution+30 µM AMPA (2 s application time, 30 s interval between applications) repeated until measurements were stable.

2) Test current—exchange from extracellular solution+10 nM of compound of invention to extracellular solution+10 nM of compound of invention+30 µM AMPA (2 s application time, 30 s interval between applications) repeated until measurements were stable. All experiments were performed at ambient temperature (21 to 24° C.).

The activity of a compound of the invention was determined by measuring the area under the curve (during 2 s period of application) for the 30 µM AMPA response in the presence of the compound of the invention and expressing it as % of potentiation of the 30 µM AMPA alone response (30 µM AMPA in the absence of the compound of the invention).

Some of the Example compounds of the invention were tested in this assay and the mean responses at 10 nM showed a range of 95% to 148% increase of response of 30 μM AMPA alone, and at 10 μM showed a range of 160% to 440% increase of response of 30 μM AMPA alone.

Electrophysiological Activity at Human Recombinant GluR21 Homomeric AMPARs

Response to 1 mM glutamate in the presence of compound was normalized against the response in the absence of compound that is considered 100%. Glutamate was applied for 2 seconds pulse every 30 seconds. Currents analysis was performed after data acquisition and using zero subtraction function (leak subtraction) measuring the net charge (time integration of the current) in the first 2000 ms from the onset of the peak and measuring the peak amplitude. If run-up or run-down was observed, extrapolation of control values was performed using pre and post drug control data. In the analysis the average of current amplitudes or charge transfer measurements was calculated considering only currents after the stabilization of the signal (when the equilibrium was reached). Potentiation of charge transfer and peak current amplitude was measured after application of 100 nM and 10 μM of the test compound. The activity of a compound of the invention was determined by measuring the area under the curve (during 2 s period of application) for the 1 mM glutamate challenge in the presence of the compound of the invention and expressing it as % of potentiation of the 1 mM glutamate challenge alone (1 mM glutamate in the absence of the compound of the invention).

Some of the Example compounds of the invention were tested in this assay and the mean responses at 100 nM showed a range of 102% to 172% potentiation of the 1 mM glutamate challenge alone, and mean responses at 10 μM showed a range of 576% to 2868% potentiation of the 1 mM glutamate challenge alone.

The invention claimed is:

1. A compound of formula (I) or a salt thereof:

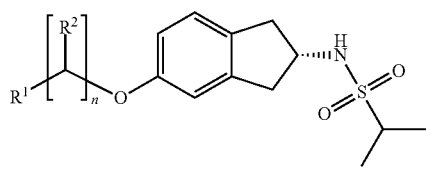

wherein:
n is 0, 1, 2 or 3;
$R^1$ is selected from phenyl and pyridyl, each of which is optionally substituted by one or two groups independently selected from $C_{1-4}$alkyl and halogen; and
$R^2$ is selected from H and $CH_3$ when n is 1 and $R^2$ is H when n is 2 or 3.

2. A compound as claimed in claim 1, wherein n is 0.

3. A compound as claimed in claim 1, wherein $R^2$ is H and n is 1, 2 or 3.

4. A compound as claimed in claim 1, wherein $R^1$ is pyridyl optionally substituted by a halogen or by one or two $C_{1-4}$alkyl.

5. A compound which is:
N-[(2S)-5-(phenyloxy)-2,3-dihydro-1H-inden-2-yl]-2-propanesulfonamide;
N-{(2S)-5-[(6-methyl-3-pyridinyl)oxy]-2,3-dihydro-1H-inden-2-yl}-2-propanesulfonamide;
N-[(2S)-5-(2-pyridinyloxy)-2,3-dihydro-1H-inden-2-yl]-2-propanesulfonamide;
N-{(2S)-5-[(5-fluoro-2-pyridinyl)oxy]-2,3-dihydro-1H-inden-2-yl}-2-propanesulfonamide;
N-{(2S)-5-[(2-methyl-3-pyridinyl)oxy]-2,3-dihydro-1H-inden-2-yl}-2-propanesulfonamide;
N-{(2S)-5-[(4-methyl-3-pyridinyl)oxy]-2,3-dihydro-1H-inden-2-yl}-2-propanesulfonamide;
N-{(2S)-5-[(6-methyl-2-pyridinyl)oxy]-2,3-dihydro-1H-inden-2-yl}-2-propanesulfonamide;
N-{(2S)-5-[(5-methyl-2-pyridinyl)oxy]-2,3-dihydro-1H-inden-2-yl}-2-propanesulfonamide;
N-{(2S)-5-[(4-methyl-2-pyridinyl)oxy]-2,3-dihydro-1H-inden-2-yl}-2-propanesulfonamide;
or a salt thereof.

6. A compound which is:
N-{(2S)-5-[(2-pyridinylmethyl)oxy]-2,3-dihydro-1H-inden-2-yl}-2-propanesulfonamide;
N-((2S)-5-{[(2-methyl-3-pyridinyl)methyl]oxy}-2,3-dihydro-1H-inden-2-yl)-2-propanesulfonamide;
N-((2S)-5-{[(6-methyl-3-pyridinyl)methyl]oxy}-2,3-dihydro-1H-inden-2-yl)-2-propanesulfonamide;
N-{(2S)-5-[(3-pyridinylmethyl)oxy]-2,3-dihydro-1H-inden-2-yl}-2-propanesulfonamide;
N-((2S)-5-{[3-(3-pyridinyl)propyl]oxy}-2,3-dihydro-1H-inden-2-yl)-2-propanesulfonamide;
N-((2S)-5-{[3-(6-methyl-3-pyridinyl)propyl]oxy}-2,3-dihydro-1H-inden-2-yl)-2-propanesulfonamide;
N-((2S)-5-{[2-(3-pyridinyl)ethyl]oxy}-2,3-dihydro-1H-inden-2-yl)-2-propanesulfonamide;
N-((2S)-5-{[(2,6-dimethyl-3-pyridinyl)methyl]oxy}-2,3-dihydro-1H-inden-2-yl)-2-propanesulfonamide;
N-{(2S)-5-[(4-pyridinylmethyl)oxy]-2,3-dihydro-1H-inden-2-yl}-2-propanesulfonamide;
N-((2S)-5-{[(2-methyl-4-pyridinyl)methyl]oxy}-2,3-dihydro-1H-inden-2-yl)-2-propanesulfonamide;
N-((2S)-5-{[(1S)-1-(6-methyl-3-pyridinyl)ethyl]oxy}-2,3-dihydro-1H-inden-2-yl)-2-propanesulfonamide;
N-((2S)-5-{[(1R)-1-(6-methyl-3-pyridinyl)ethyl]oxy}-2,3-dihydro-1H-inden-2-yl)-2-propanesulfonamide;
or a salt thereof.

7. A compound as claimed in claim 1 or a pharmaceutically acceptable salt thereof.

8. A pharmaceutical composition comprising a compound as defined in claim 7 and at least one pharmaceutically acceptable carrier or diluent.

9. A combination product comprising a compound as defined in claim 7 and an antipsychotic.

* * * * *